US008385560B2

(12) United States Patent
Solbeck et al.

(10) Patent No.: US 8,385,560 B2
(45) Date of Patent: Feb. 26, 2013

(54) IN-EAR DIGITAL ELECTRONIC NOISE CANCELLING AND COMMUNICATION DEVICE

(76) Inventors: Jason Solbeck, Canaan, NH (US); Matt Maher, West Lebanon, NH (US); Christopher Deitrich, Hartland, VT (US); Laura Ray, Hanover, NH (US)

( * ) Notice: Subject to any disclaimer, the term of this patent is extended or adjusted under 35 U.S.C. 154(b) by 1168 days.

(21) Appl. No.: 12/236,657

(22) Filed: Sep. 24, 2008

(65) Prior Publication Data

US 2009/0080670 A1 Mar. 26, 2009

Related U.S. Application Data

(60) Provisional application No. 60/974,624, filed on Sep. 24, 2007.

(51) Int. Cl.
*G10K 11/16* (2006.01)
*A61F 11/06* (2006.01)

(52) U.S. Cl. ................... 381/71.8; 381/71.12; 381/71.1; 381/72

(58) Field of Classification Search ................. 381/71.1, 381/71.6–71.14, 72, 74, 317; 181/130, 135
See application file for complete search history.

(56) References Cited

U.S. PATENT DOCUMENTS

| | | | | |
|---|---|---|---|---|
| 4,985,925 | A | 1/1991 | Langberg et al. | 387/72 |
| 5,577,511 | A | 11/1996 | Killion | 128/746 |
| 6,310,961 | B1 | 10/2001 | Oliveira et al. | 381/328 |
| 6,415,034 | B1 * | 7/2002 | Hietanen | 381/71.6 |
| 6,567,524 | B1 * | 5/2003 | Svean et al. | 381/71.1 |
| 6,741,707 | B2 | 5/2004 | Ray et al. | 381/71.11 |
| 6,996,241 | B2 | 2/2006 | Ray et al. | 381/71.11 |
| 7,039,195 | B1 | 5/2006 | Svean et al. | 381/71.6 |
| 8,059,847 | B2 * | 11/2011 | Nordahn | 381/328 |
| 2010/0272270 | A1 * | 10/2010 | Chaikin et al. | 381/59 |

FOREIGN PATENT DOCUMENTS

| | | | |
|---|---|---|---|
| EP | 0684750 | A2 | 11/1995 |
| GB | 2184629 | A | 6/1987 |

OTHER PUBLICATIONS

European Patent Office, International Search Report, dated Dec. 16, 2008, PCT/US2008/077441.
Lucke, Andreas, Regional Phase in Europe based on PCT/US2008/077441, European Patent Application No. 08 832 872.9, Apr. 21, 2010, 11 pages.
European Patent Office, Communication pursuant to Article 94(3) EPC, European Patent Application No. 08 832 872.9, Aug. 1, 2011, 10 pages.
Ray, Laura et al., Hybrid feedforward-feedback active noise reduction for hearing protection and communication, J. Acoust. Soc. Am. 120 (4), Oct. 2006, pp. 2026-2036.

(Continued)

*Primary Examiner* — Ryan Johnson
(74) *Attorney, Agent, or Firm* — Sunstein Kann Murphy & Timbers LLP

(57) ABSTRACT

A noise canceling and communication system includes an in-ear device adapted to fit in the ear canal of a device user. A passive noise reduction element reduces external noise entering the ear canal. An external microphone senses an external acoustic signal outside the ear canal. An internal microphone senses an internal acoustic signal proximal to the tympanic membrane. One or more internal sound generators produce a noise cancellation signal and an acoustic communication signal, both directed towards the tympanic membrane. A probe tube shapes an acoustic response between the internal sound generator and the internal microphone to be relatively constant over a wide audio frequency band. An electronics module is located externally of the ear canal and in communication with the in-ear device for processing the microphone signals using a hybrid feed forward and feedback active noise reduction algorithm to produce the noise cancellation signal.

14 Claims, 28 Drawing Sheets

OTHER PUBLICATIONS

Streeter, Alexander et al., Hybrid Feedforward-Feedback Active Noise Control, Proceeding of the 2004 American Control Conference, Boston, Massachusetts Jun. 30-Jul. 2, 2004, pp. 2876-2881.

Lucke, Andreas, Response to Aug. 1, 2011 Communication pursuant to Article 94(3) EPC in European Patent Application No. 08 832 872.9, Feb. 13, 2012, 22 pages.

* cited by examiner

IN-EAR DIGITAL ELECTRONIC NOISE CANCELLING AND COMMUNICATION DEVICE

This application claims priority from U.S. Provisional Patent Application 60/974,624, filed Sep. 24, 2007, hereby incorporated by reference.

STATEMENT REGARDING FEDERALLY SPONSORED RESEARCH OR DEVELOPMENT: This invention was made with government support under contract W81XWH-05-C-0031 awarded by the Department of Defense (US Army Medical Research) and also under contract FA8902-07-C-1008 awarded by the Department of Defense (US Air Force Materiel Command). The government has certain rights in the invention.

FIELD OF THE INVENTION

The invention is directed to an in-ear device for working in high-noise environments, and more specifically, to a communications device for use in a high-noise environment.

BACKGROUND ART

Many military and occupational trades require that personnel work in a high-noise environment which makes communications difficult and also can cause noise-induced hearing loss. To avoid hearing loss, hearing protection is worn, which unfortunately also compromises the ability to communicate effectively or hear warning signals and cues. Some passive in-ear hearing protection systems exist, a few systems combine passive hearing protection with in-ear delivery of a communication signal, a small number of such combined systems also incorporate active noise reduction. Some hearing protectors, e.g., those used in commercial and military aviation, include a radio channel for communication. But in high noise environments, speech intelligibility in radio communications is compromised by residual noise within the volume between the hearing protector and the tympanic membrane.

SUMMARY OF THE INVENTION

Embodiments of the present invention are directed to a noise canceling and communication device. An in-ear device is adapted to fit in the ear canal of a device user. A passive noise reduction element reduces external noise entering the ear canal. An external microphone senses an external acoustic signal outside the ear canal to produce a representative external microphone signal. An internal microphone senses an internal acoustic signal proximal to the tympanic membrane to produce a representative internal microphone signal. An internal sound generator produces a noise cancellation signal and an acoustic communication signal, both directed towards the tympanic membrane. A probe tube shapes an acoustic response between the internal sound generator and the internal microphone to be relatively constant over a wide audio frequency band. An electronics module is located externally of the ear canal and in communication with the in-ear device for processing the microphone signals using a hybrid feed forward and feedback active noise reduction algorithm to produce the noise cancellation signal. The noise reduction algorithm includes a modeling component based on a transfer function associated with the internal sound generator and at least one of the microphones to automatically adjust the noise cancellation signal for fit and geometry of the ear canal of the user. The communication component also includes a modeling component based on a transfer function associated with the internal sound generator and at least one of the microphones to automatically adjust the communication signal for fit and geometry of the ear canal of the user and to assure that the communication signal does not interfere with the noise reduction algorithm and that the noise cancellation signal does not interfere with passing of the communication signal.

The electronics module may further pass through or produce the communication signal for the internal sound generator. The noise reduction algorithm may reject physiological or voice generated noise present in the ear canal. The noise reduction algorithm may include a band pass filtering component for directing acoustic energy of the noise cancellation signal to selected frequency bands. The noise reduction algorithm may be implemented on a Field-Programmable Gate Array (FPGA) as a state machine using VHSIC Hardware Description Language (VHDL) programming language and/or be implemented with a combination of VHSIC Hardware Description Language (VHDL) programming language and assembly code.

In further specific embodiments, the probe tube may include a probe tube outlet which is replaceable so as to keep the probe tube free of cerumen. The probe tube may be acoustically isolated from the internal sound generator and/or the internal microphone. A noise exposure sensing module may determine a time-weighted noise exposure of the device user. The in-ear device may include a molded plastic device housing encapsulating electronic components of the in-ear device.

In a further embodiment, the internal sound generator may include a noise cancellation sound generator for generating the noise cancellation signal and a separate communication sound generator for generating the acoustic communication signal, thereby contributing to fail-safe communications.

Embodiments of the present invention also include an in-ear communication device adapted to fit in the ear canal of a device user. A passive noise reduction element fits in the ear canal of the user for reducing external noise entering the ear canal. A sensing element generates a sensing data signal associated with the ear canal. A probe tube has one end coupled to the sensing element and the other end having a probe tube outlet proximal to the tympanic membrane for shaping the data input to the sensing element. In a further such embodiment, the probe tube outlet may be replaceable so as to keep the probe tube free of cerumen.

DETAILED DESCRIPTION OF SPECIFIC EMBODIMENTS

Embodiments of the present invention are directed to a noise canceling and communication system having two major components: (1) an in-ear device that fits into the ear canal of a device user, and (2) an electronics module located outside the ear canal and in communication with the in-ear device. The electronics module processes multiple microphone signals using a hybrid feed forward and feedback active noise reduction algorithm to produce a noise cancellation signal that automatically adjusts to the fit and geometry of the ear canal. The electronics module includes analog circuitry for signal conditioning, data conversion, power management, and a programmable digital processor for additional signal processing and application of the noise reduction algorithm. The electronics module may pass a communication signal to the in ear device.

Figure 1:
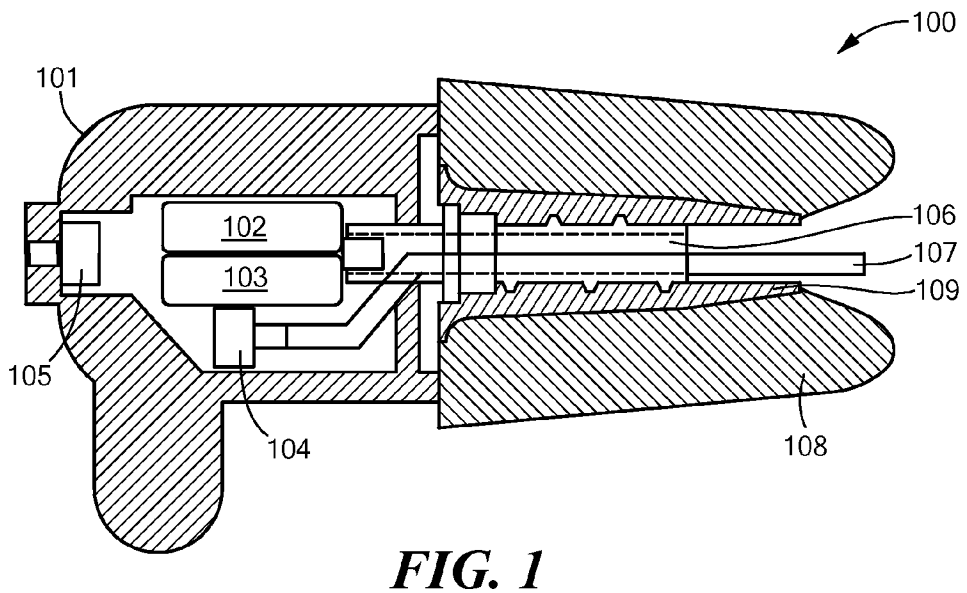
FIG. 1 shows a schematic cross-section of an embodiment of an in-ear device having two sound generators.

FIG. 1 shows a cross-sectional view of an embodiment of a noise canceling in-ear device 100 having a molded plastic body 101 which includes a soft resilient ear tip 108 (e.g., foam, silicone, etc.) that acts as a passive noise reduction element for reducing external noise entering the ear canal. The ear tip 108 provides acoustic sealing between the auditory meatus of the ear canal and the tympanic membrane of the device user. The plastic body 101 includes an outer opening for at least one external microphone 105 that senses an external acoustic signal outside the ear canal to produce a representative external microphone signal. An internal microphone 104 senses an internal acoustic signal via probe tube 107 which opens proximal to the tympanic membrane and from that produces a representative internal microphone signal. Internal structures of the in-ear device 100 may be incorporated into the plastic body 101 through a low-temperature and pressure injection-molding process that encapsulates and provides strain relief to the components, wires, and connections.

An internal sound generating arrangement includes a noise cancellation sound generator 102 for producing a noise cancellation signal created by the external electronics module using the noise reduction algorithm. A communications sound generator 103 produces an acoustic communication signal from an external communication channel such as a radio communications system, or from an external voice signal sensed by the external microphone 105. The communication signal may be passed through the electronics module or passed through directly to the in-ear device.

Figure 2:
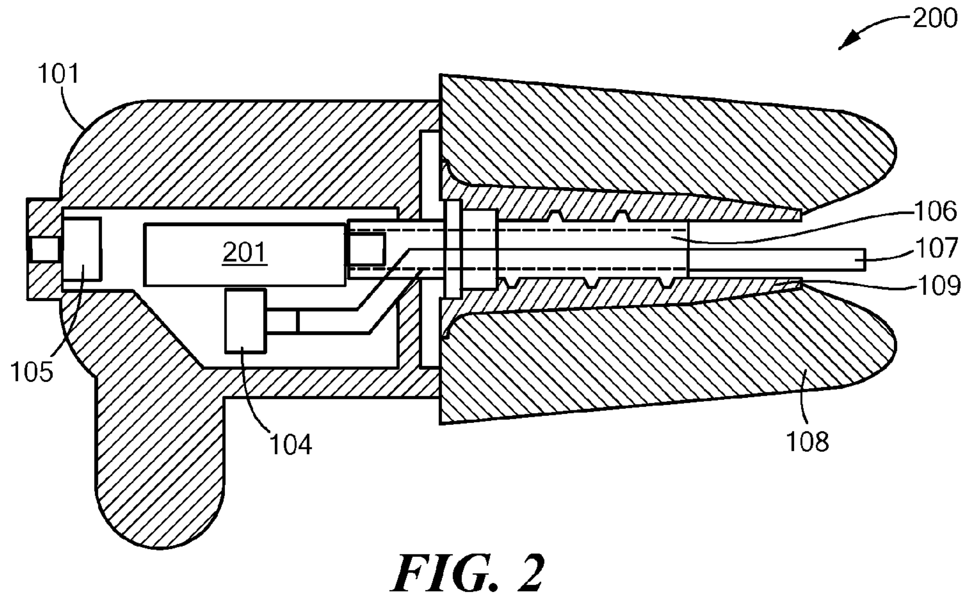
FIG. 2 shows a schematic cross-section of an embodiment of an in-ear device having one sound generator.

A dual sound generator configuration allows the frequency response of the communications sound generator 103 to be tuned to the frequency band of the human voice and the frequency response of the noise cancellation generator 102 to be tuned to the frequency band of the noise. This configuration also decouples the communications channel and the noise cancellation channel so that fail-safe communication is provided. That is, if the noise cancellation fails for any reason, radio communication is retained along with the passive noise attenuation provided by the in-ear device 100. FIG. 2 shows a cross-sectional view of an alternate embodiment of an in-ear device 200 having a single sound generator 201 for producing both the noise cancellation signal and the acoustic communication signal.

A hollow ear tip adapter 106 is threaded or press-fit over a hollow center post 109 within the ear tip 108. Ear tip adapter 106 has a space at its base for acoustically summing the two sound generator signals to produce a hybrid noise-reduced acoustic communication signal directed to the tympanic membrane. The diameter and length of the probe tube 107 and the diameter and length of the ear tip adaptor 106 affect a transfer function between the noise cancellation sound generator 102 and the internal microphone 104. This allows high-performance digital feedback compensation to extend the frequency band of noise cancellation to at least 1000 Hz with flat response and minimal resonance. In another embodiment, rather than a probe tube 107 as such, an internal acoustic sensing arrangement may be based on a split ear tip adapter with a center well dividing the acoustic space into two separate chambers, one for delivering the hybrid noise-reduced acoustic communication signal into the ear canal, and the other for coupling an internal acoustic signal back to the internal microphone 104.

Software for the electronics module may include one or more of: an automated methodology for measuring the transfer function between the sound generators 102 and 103 and the internal microphone 104 (cancellation path and communication path) and between the sound generators 102 and 103 and the external microphone 105 (feedback path); a hybrid feed forward-feedback noise canceling algorithm; signal processing for band pass filtering of the microphone signals to direct the sound generator energy to the desired frequency bands; band pass filtering within the noise reduction algorithm for rejecting physiological or voice generated noise conducted into the sealed space between the meatus and the tympanic membrane; an external communications algorithm for passing an external communication signal to the user through detection of the communication signal at the external microphone 105 and noise filtering of the communication signal and delivery to the user through the communications sound generator 103; a noise exposure algorithm for measuring time-weighted noise exposure of the user; and a sealing algorithm for detecting whether a proper seal condition exists in the ear canal. The noise cancellation algorithm accommodates the variation in the cancellation path and communication path transfer functions due to individual meatus and ear canal geometries and uses the feedback transfer function to detect an improper seal condition.

Figure 3:
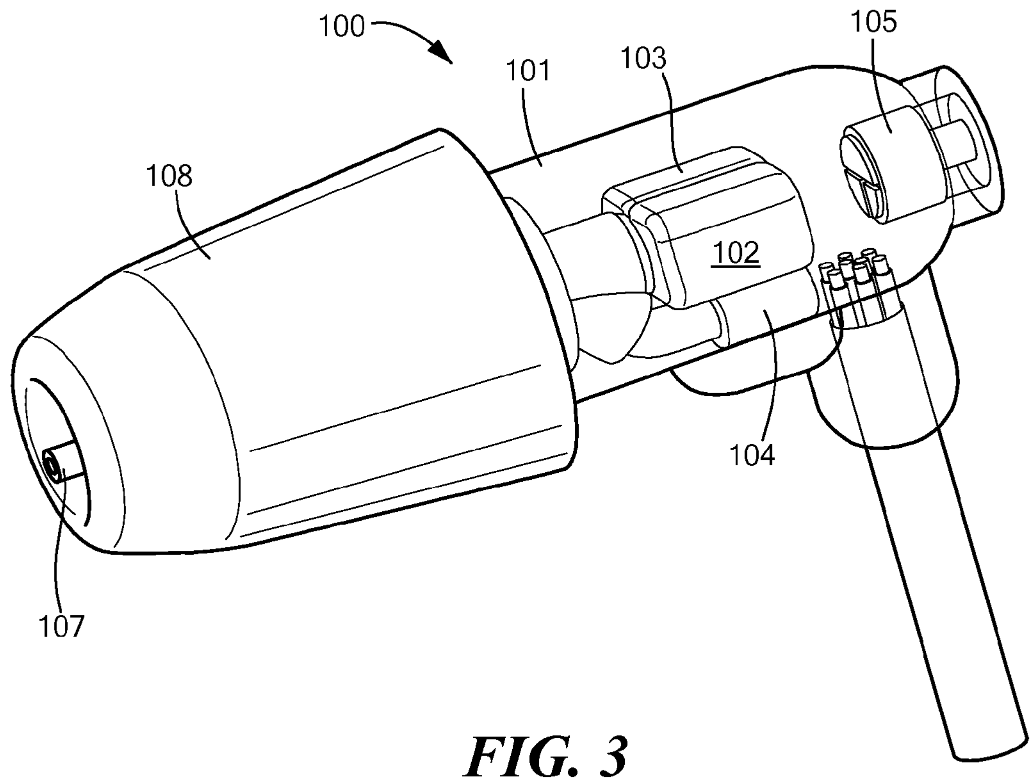
FIG. 3 shows a CAD drawing of an embodiment according to FIG. 1.
Figure 4:
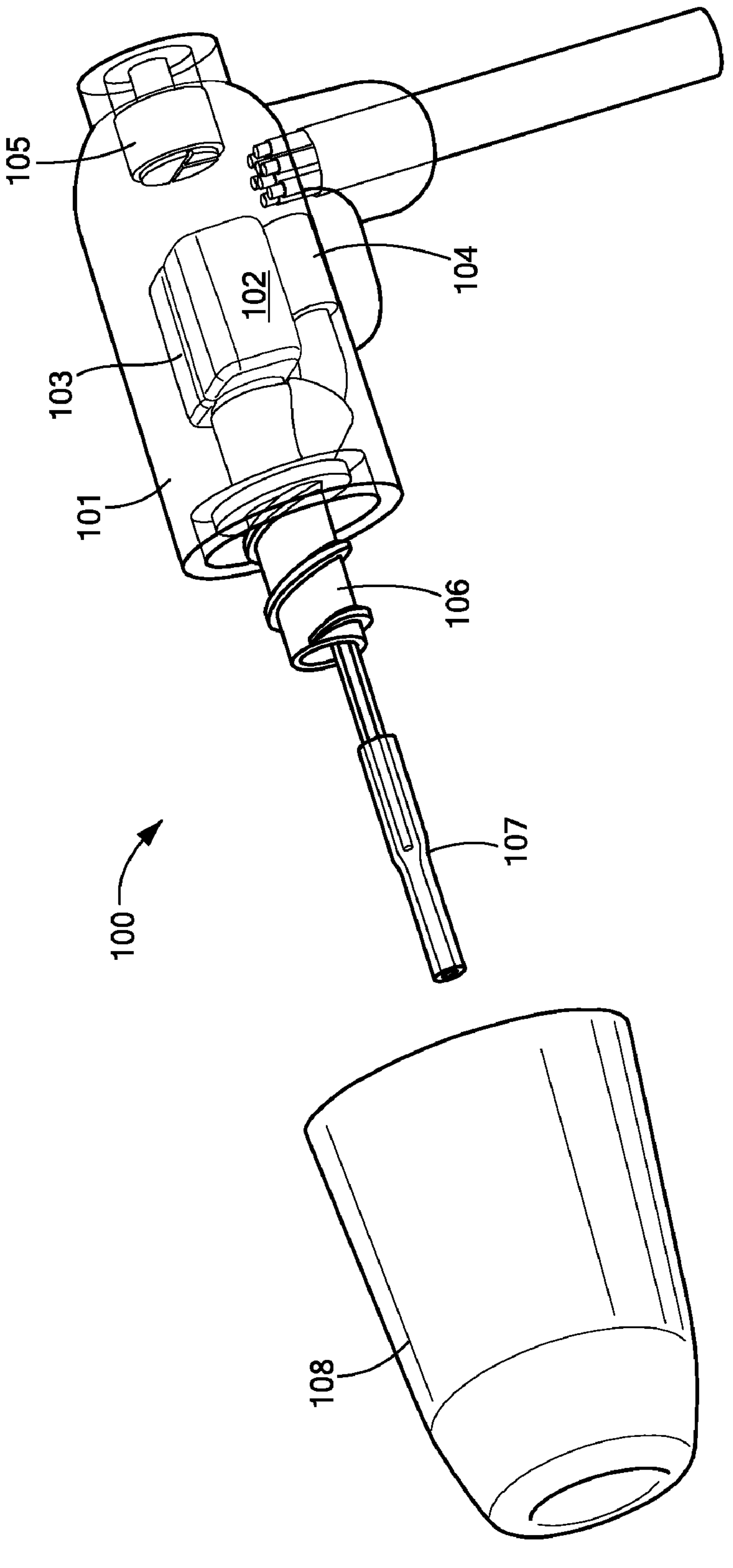
FIG. 4 shows an exploded view of the embodiment in FIG. 3.
Figure 5:
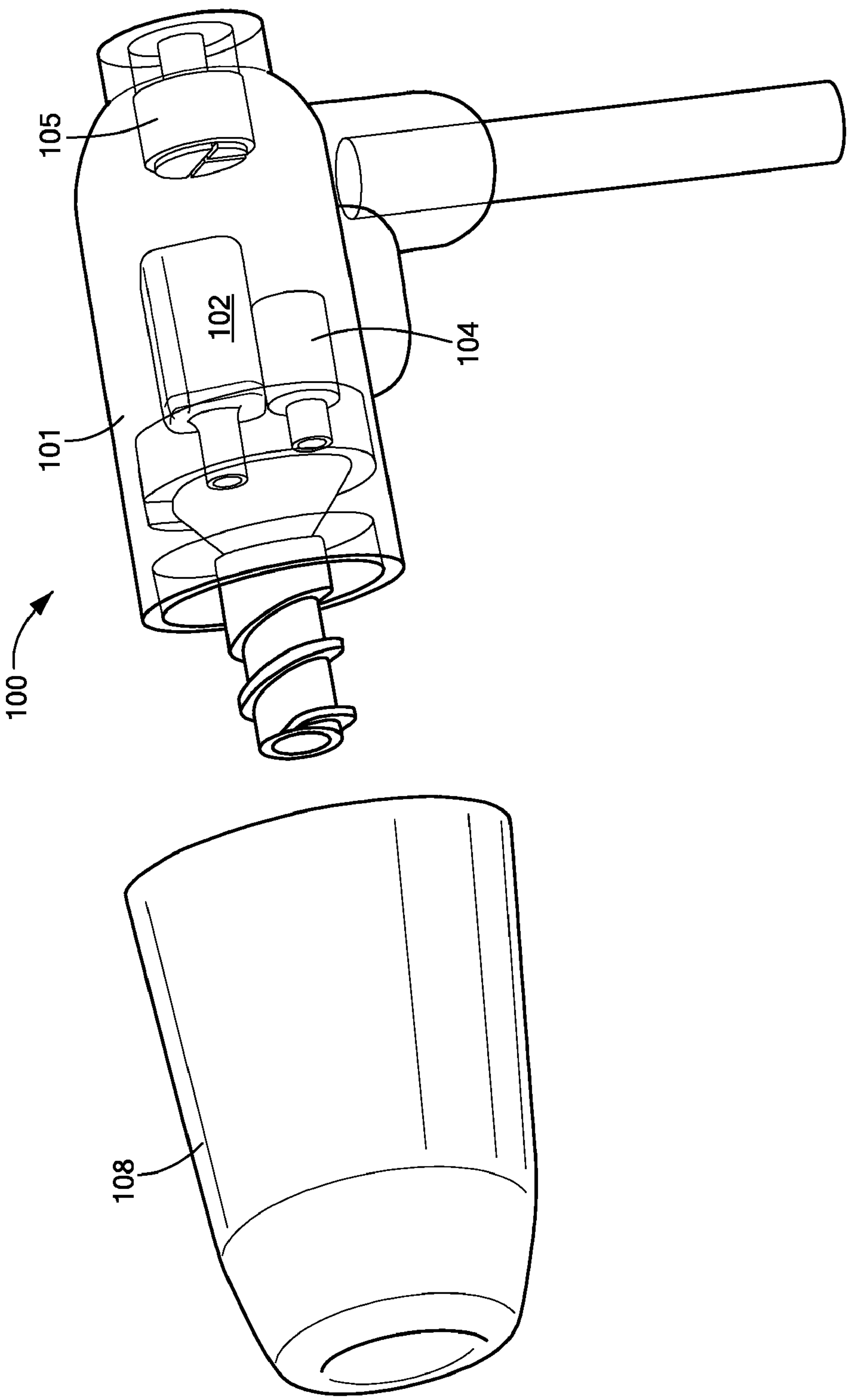
FIG. 5 shows an exploded view of an embodiment of FIG. 1 using an alternate ear tip adapter.
Figure 6:
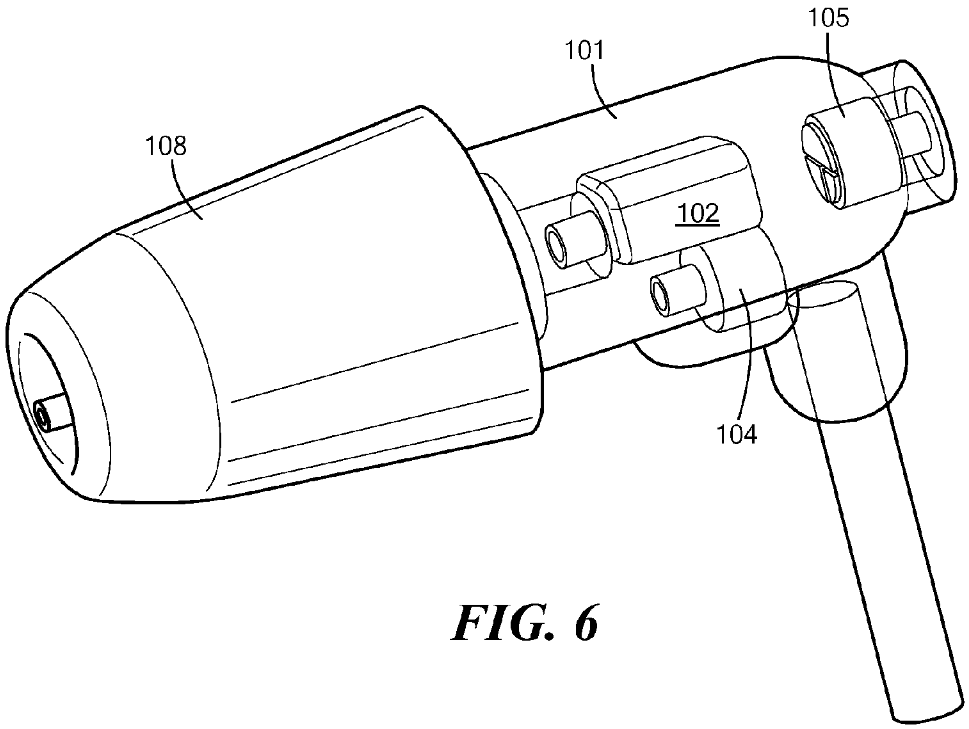
FIG. 6 shows a CAD drawing of an embodiment of an in-ear device having a single sound generator as in FIG. 2, with ear tip adaptor removed to show component placement.
Figure 7:
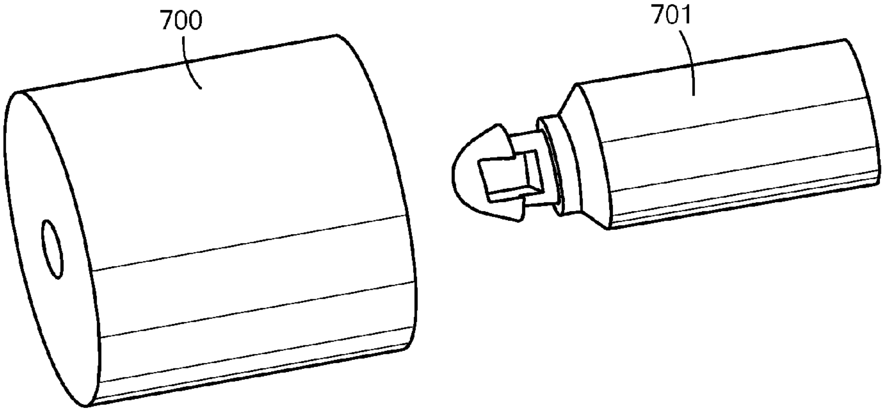
FIG. 7 shows an alternate embodiment of the ear tip of the in-ear device.

FIG. 3 shows a CAD drawing of an embodiment of an in-ear device 100 having two separate sound generators 102 and 103 as shown in FIG. 1. FIG. 4 shows an exploded view of the embodiment in FIG. 3 which better shows the probe tube 107 and the ear tip adapter 106, which extends from the in-ear device 100 and is sealed to the plastic body 101 on the opposite face. FIG. 5 shows an exploded view of an alternate embodiment of an ear tip adapter 501. FIG. 6 shows a CAD drawing of an embodiment of an in-ear device 200 having a single sound generator 201 as in FIG. 2 (without showing the ear tip adapter to better view the other structures within the device). FIG. 7 shows an alternate embodiment of a foam earplug 700 and plastic ear tip insert 701.

Figure 8A:
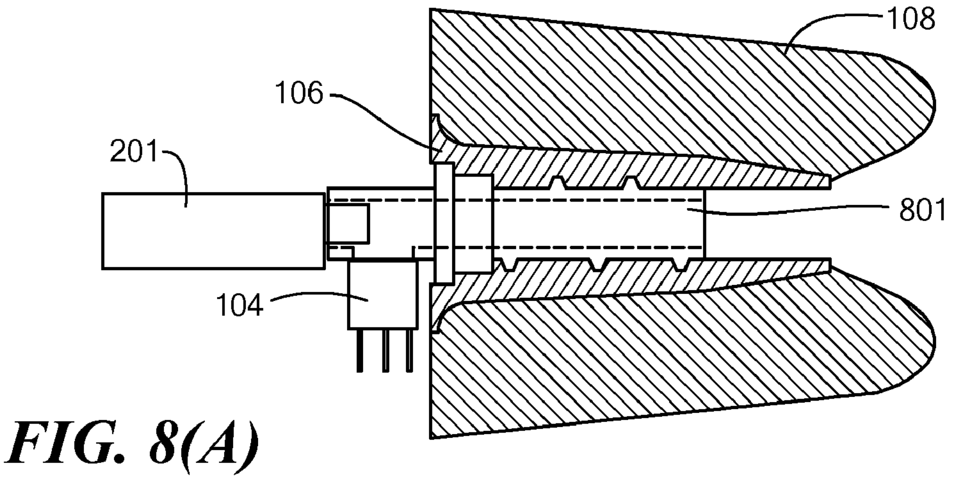
FIG. 8 shows cross-sectional views of three embodiments.
Figure 8B:
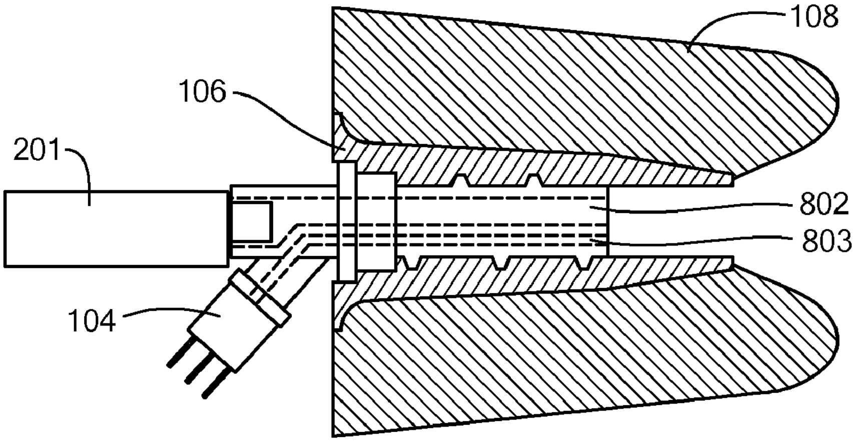
Figure 8C:
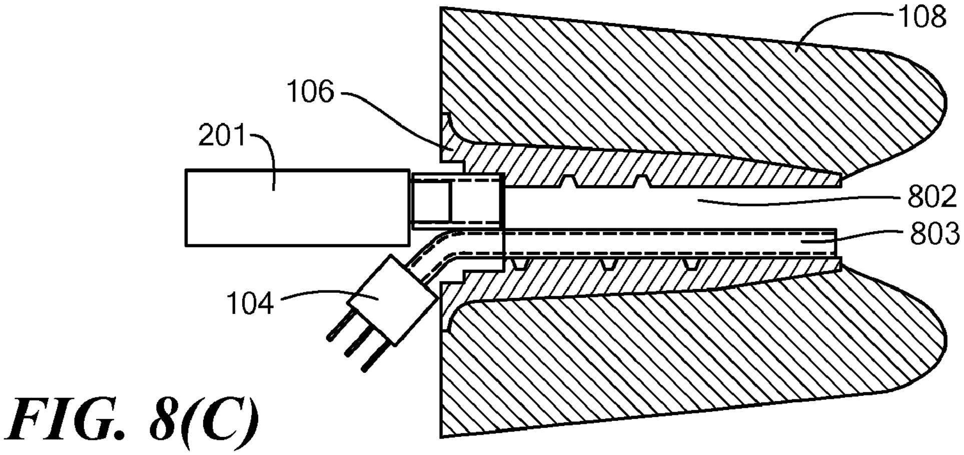
Figure 9:
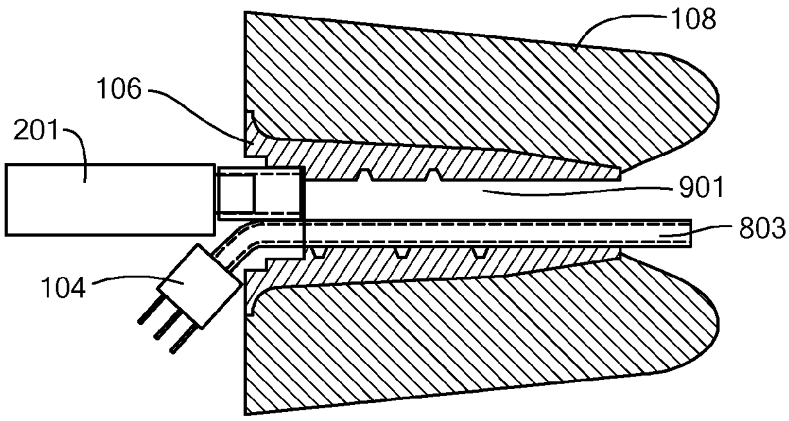
FIG. 9 shows a cross-sectional view of another embodiment.

FIG. 8 shows cross-sectional views of three different embodiments of the ear tip adaptor 106. FIG. 8A shows an embodiment having a single inner bore 801 for receiving and combining the sound generator signals towards the base of the ear tip adapter 106. To one side of the base of the inner bore 801 is the internal microphone 104 for sensing the internal microphone signal in proximity to the outlet of the sound generator 201. FIG. 8B shows another arrangement of the ear tip adapter 106 having a main bore 802 which combines and delivers the sound generator signals, and a separate small sensing bore 803 which extends part way into the main bore 802 and is coupled to the internal microphone 104. FIG. 8C shows another embodiment where the sensing bore 803 is larger and provides a different cancellation path response compared to other embodiments. so that it can extend closer to the tympanic membrane. FIG. 9 shows an embodiment having complete polymer probe tube 107 for the internal microphone 104 that extends beyond the opening of the adapter tip 106 closer still to the tympanic membrane.

Figure 10:
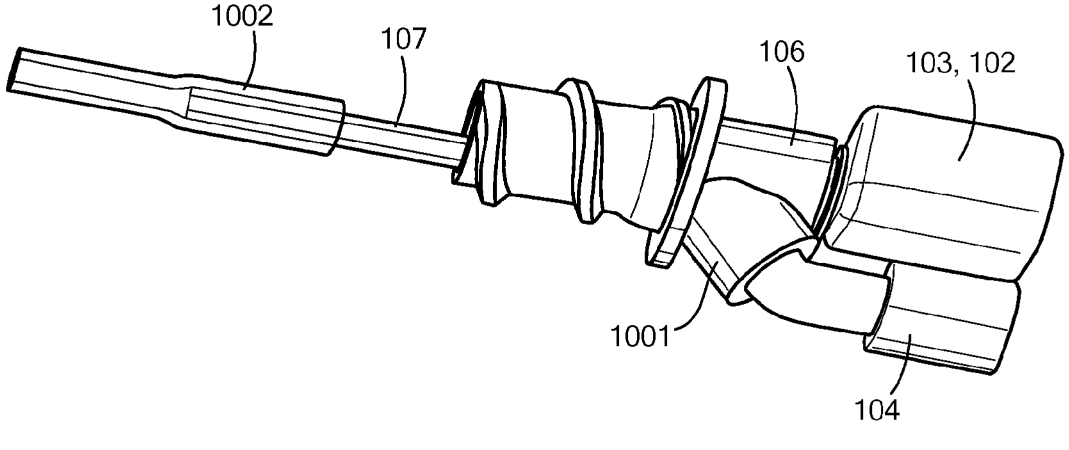
FIG. 10 shows a CAD drawing of an embodiment of the ear tip adaptor to which the sound generators and sensing element are ported according to FIG. 3.

FIG. 10 shows a CAD drawing of an embodiment of the ear tip adaptor 106 for a dual sound generator configuration as in FIG. 1. FIG. 10 shows the arrangement of the sound generators 102 and 103, ear tip adaptor 106, internal microphone 104, and probe tube 107. The sound generators 102 and 103 are ported directly to the ear tip adaptor 106. The internal microphone 104 is aligned with the sound generators 102 and 103 and ported through flexible tubing to a port 1001 on the side of the ear tip adaptor 106. Internal to the ear tip adaptor 106, a probe tube 107 is fixed to the internal microphone port 1001. A second sleeve 1002 is fixed over the probe tube 107 to provide a replaceable section that can be readily cleared of cerumen.

Figure 11:
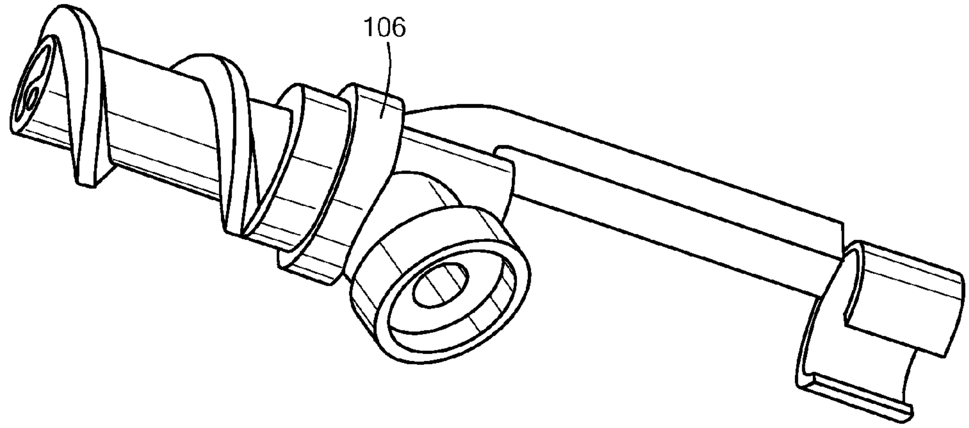
FIG. 11 shows a CAD drawing of an embodiment of the ear tip adaptor to which the sound generator is ported.

FIG. 11 shows a CAD drawing of another embodiment of the ear tip adaptor 106 to which the sound generator 201 is ported directly, through which a probe tube 107 is fastened, and to which the internal microphone 104 is ported to the probe tube 107.

Figure 12:
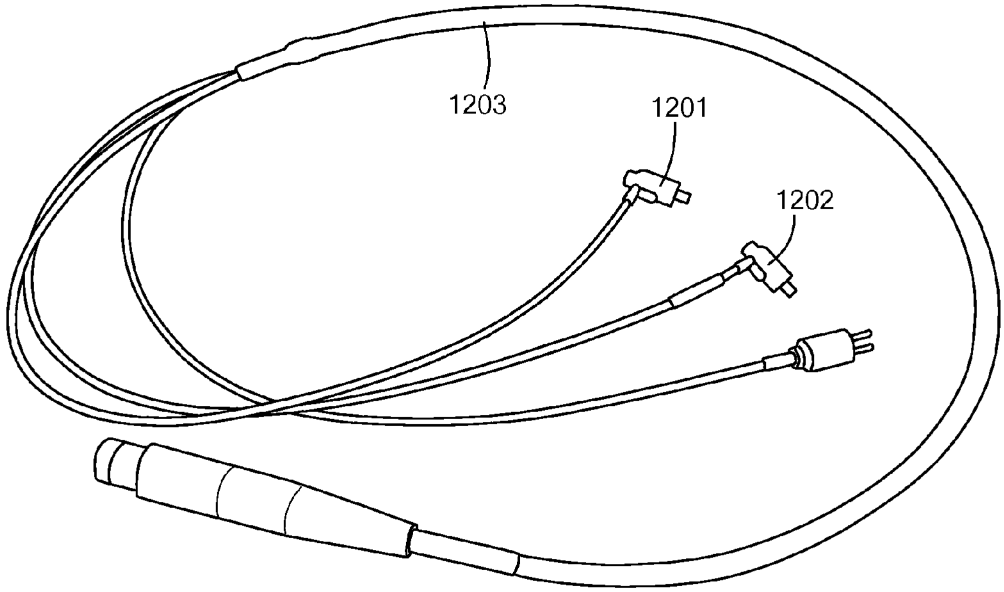
FIG. 12 shows an embodiment of an in-ear device incorporating a wiring harness and connector for four microphone signals.

FIG. 12 shows physical components of a system having two in-ear devices 1201 and 1202 incorporating a wiring harness 1203 and connector for transmitting four microphone signals (one internal microphone and one external microphone from each in-ear device) to the external electronics module, and for receiving signals from the electronics module to drive the sound generators. A separate communication channel 1204 can also deliver a signal to the communication sound generators, e.g., from a radio channel.

Figure 13:
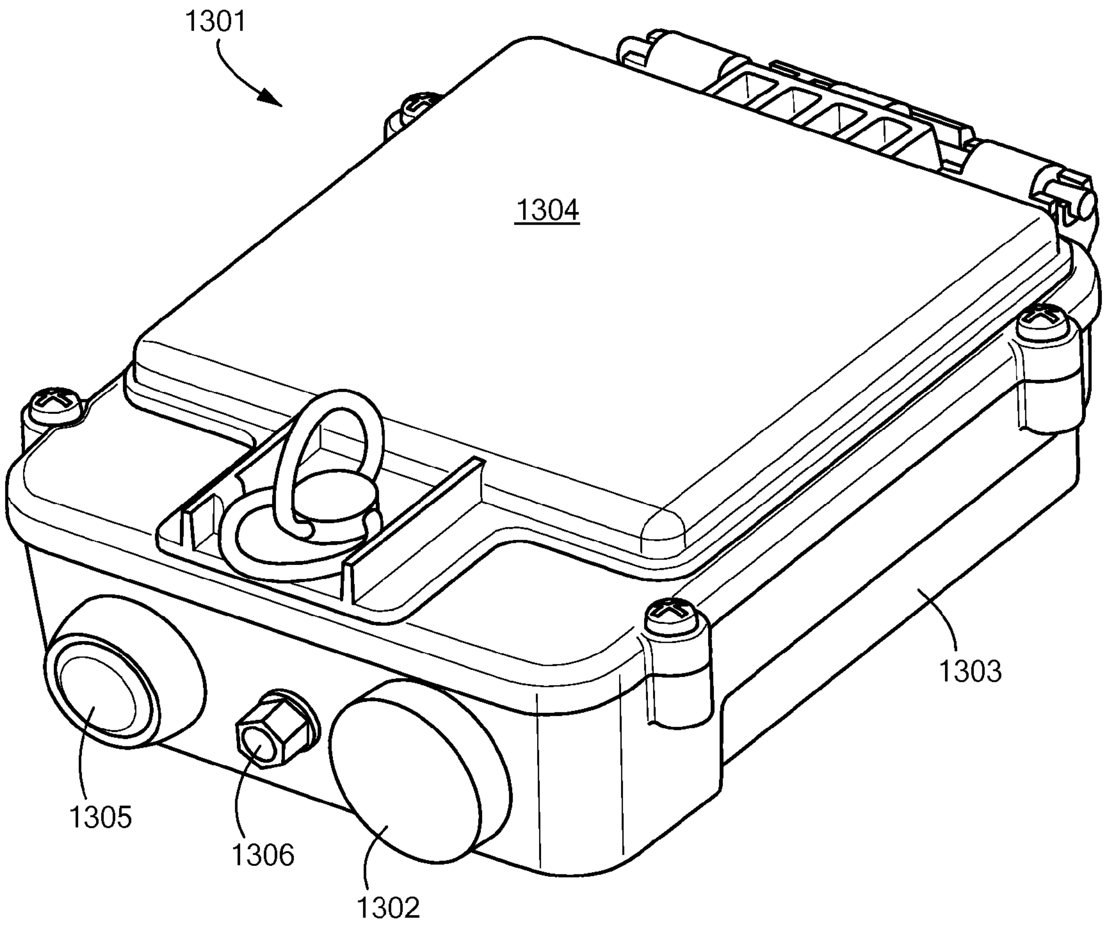
FIG. 13 shows a CAD drawing of an electronics module according to one specific embodiment.
Figure 14:
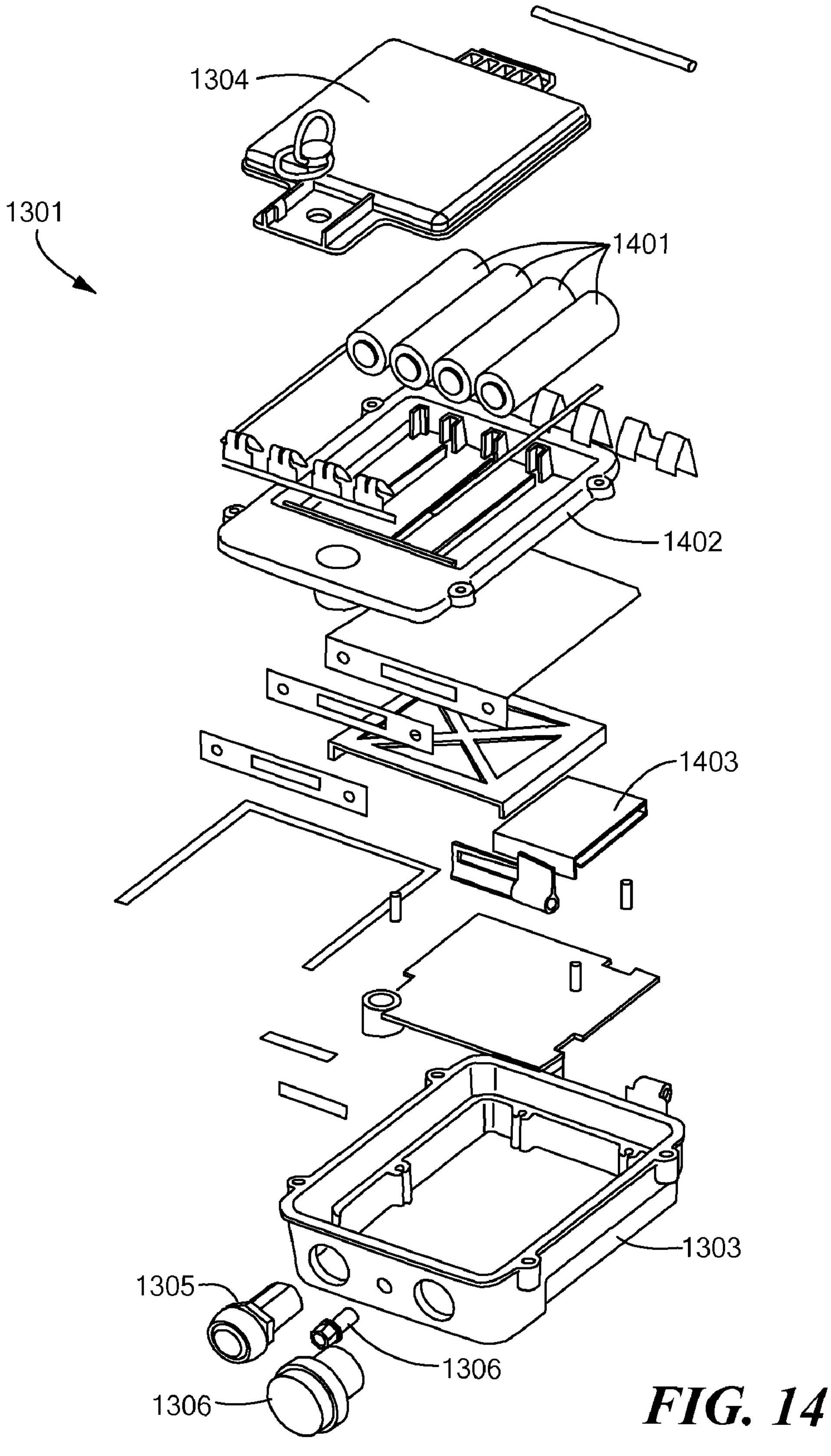
FIG. 14 shows an exploded view of the CAD drawing according to FIG. 13.
Figure 15:
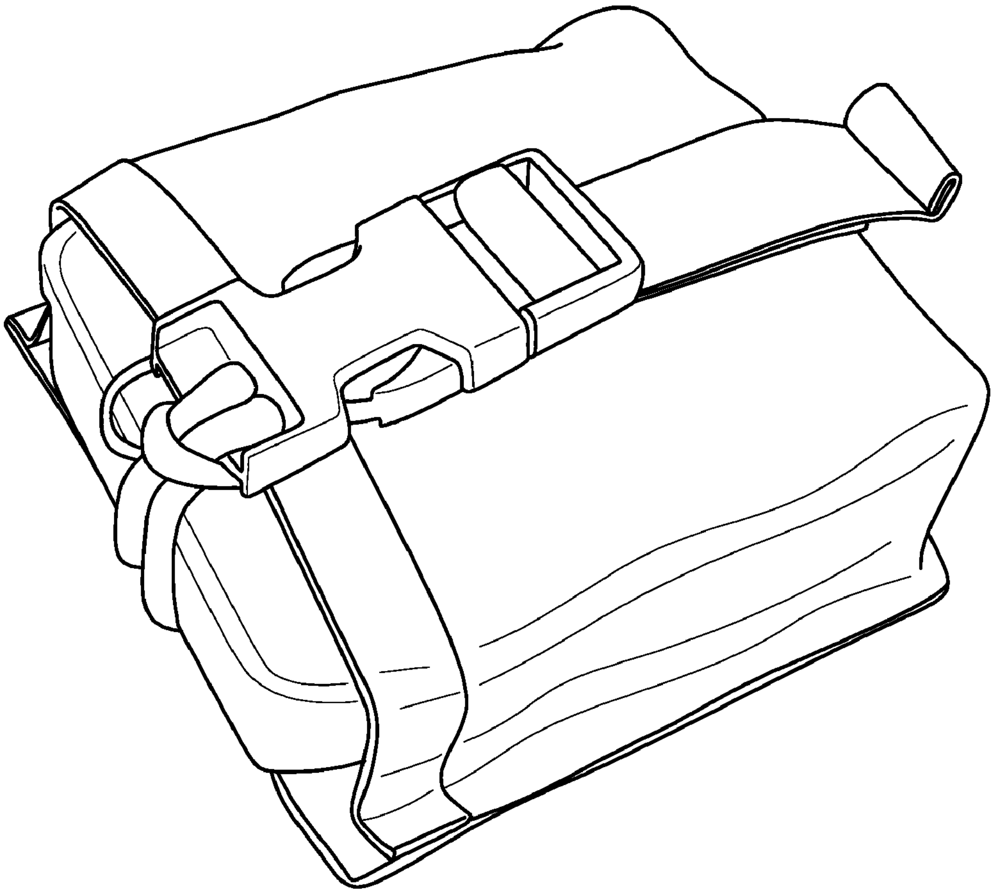
FIG. 15 shows an embodiment of the electronics module secured within a cloth pouch that attaches to a field or flight vest.

FIG. 13 shows a CAD drawing and FIG. 14 shows an exploded view of an electronics module 1301 which includes the external electronics module. Electronics module 1301 incorporates a mating connector 1302 for receiving four microphone signals (one internal and one external microphone from each of two earplugs) and transmitting signals to drive sound generators; ruggedized, plastic case 1303; top cover 1304; pushbutton on-off switch 1305; LED indicator 1306; battery 1401; battery compartment 1402 which may include power conversion and power distribution electronics; the electronics board 1403. FIG. 15 shows a photograph of an embodiment of the electronics module secured within a cloth pouch that attaches to a field or flight vest.

Figure 16:
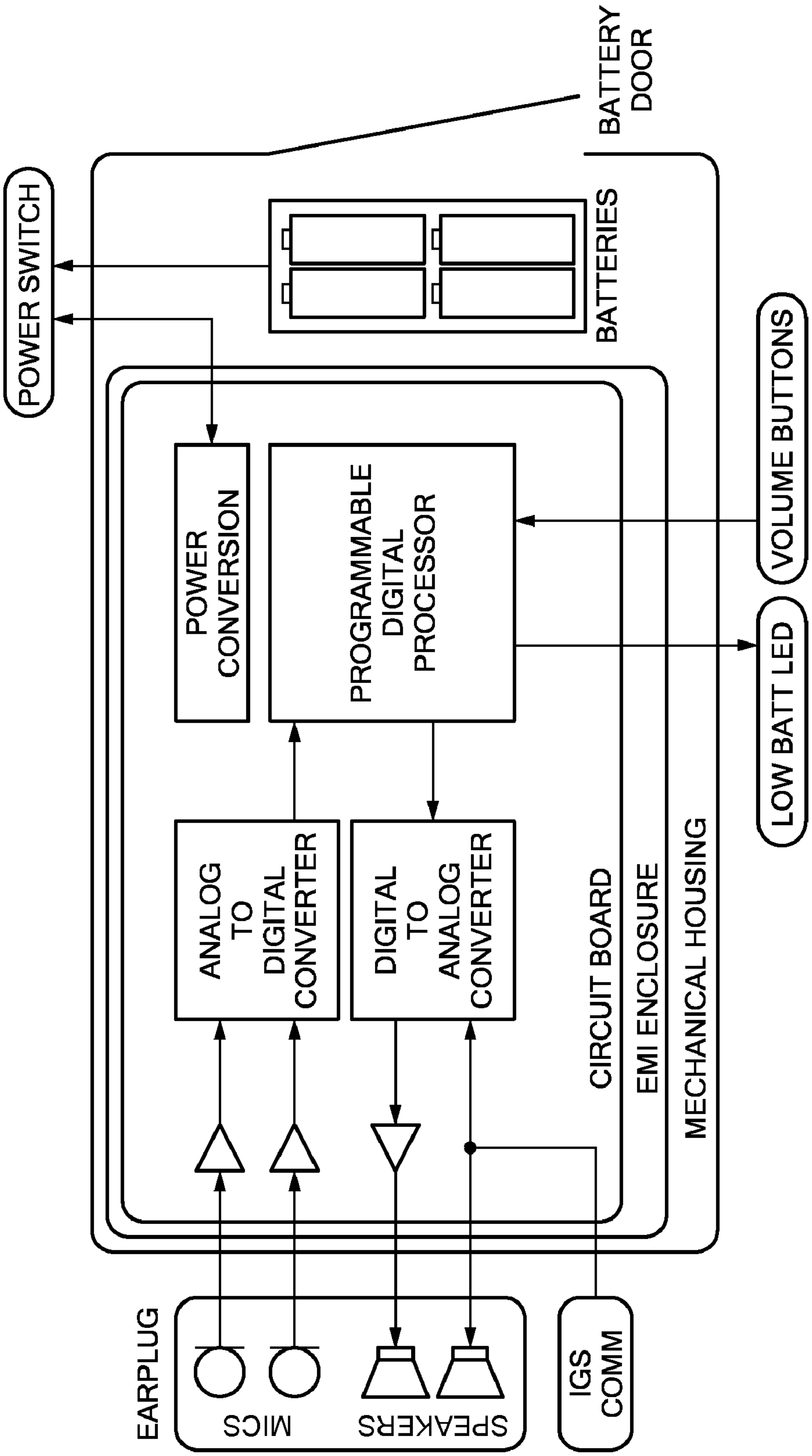
FIG. 16 shows a functional diagram of the major components of an electronics module according to one embodiment.

FIG. 16 shows a functional block diagram of the major components of the electronics module which provides signal conditioning for the microphones and sound generators; signal processing software to implement the hybrid digital feed forward-feedback active noise cancellation algorithm, automated transfer function identification, communication feed-through algorithms, and seal detection algorithms.

Figure 17:
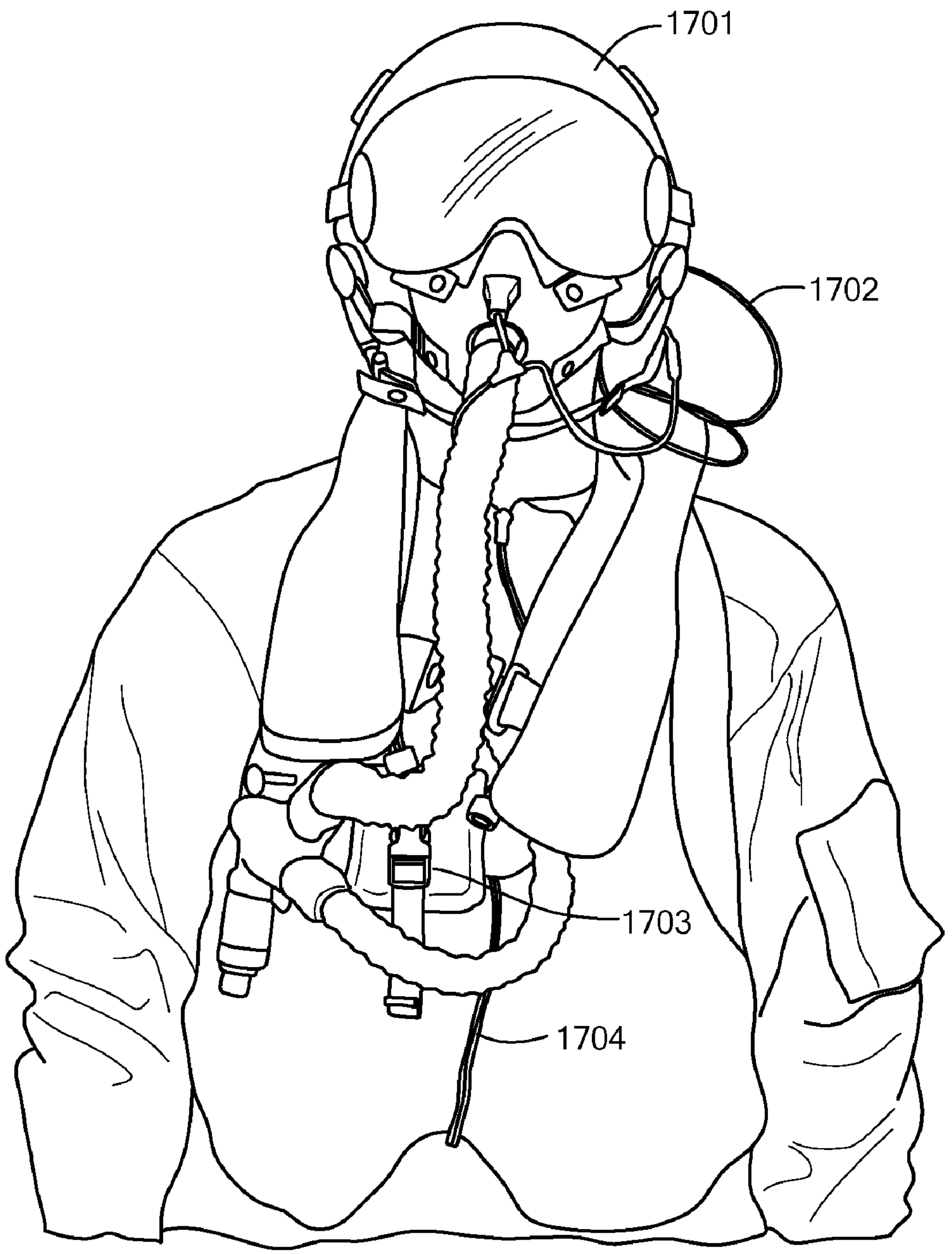
FIG. 17 illustrates an embodiment as used with a military helmet.

FIG. 17 shows an embodiment when used with a military helmet 1701, with the earplugs inserted in ears and cabling running underneath the ear cup within the helmet 1701, securing the communication cable 1702 to the back of the helmet 1701, and cabling entering the electronics module 1703 fastened to a vest through use of the cloth pouch with the black fastener and strap hanging down to the left of the zipper 1704 as shown.

The electronics module incorporates digital algorithms for one or more of measuring the cancellation path transfer function; the communication path transfer function; and the feedback path; a hybrid feed forward-feedback noise canceling algorithm; an algorithm for passing an external communication signal to the wearer through detection of the communication signal at the external microphone and noise filtering and delivery to the wearer through the communication speaker; algorithms for rejecting physiological or voice generated noise conducted into the sealed space within the meatus and tympanic membrane within the active noise cancellation algorithm; band pass filtering so as to direct the acoustic energy of the noise cancellation generator to the frequency bands of interest; electronics for passing a radio communication signal to the communication generator that are decoupled from the remaining module so as to leave communication intact should any other part of the module fail; and algorithms for measuring time-weighted noise exposure based on signals recorded at the internal microphone as detailed here.

Figure 18:
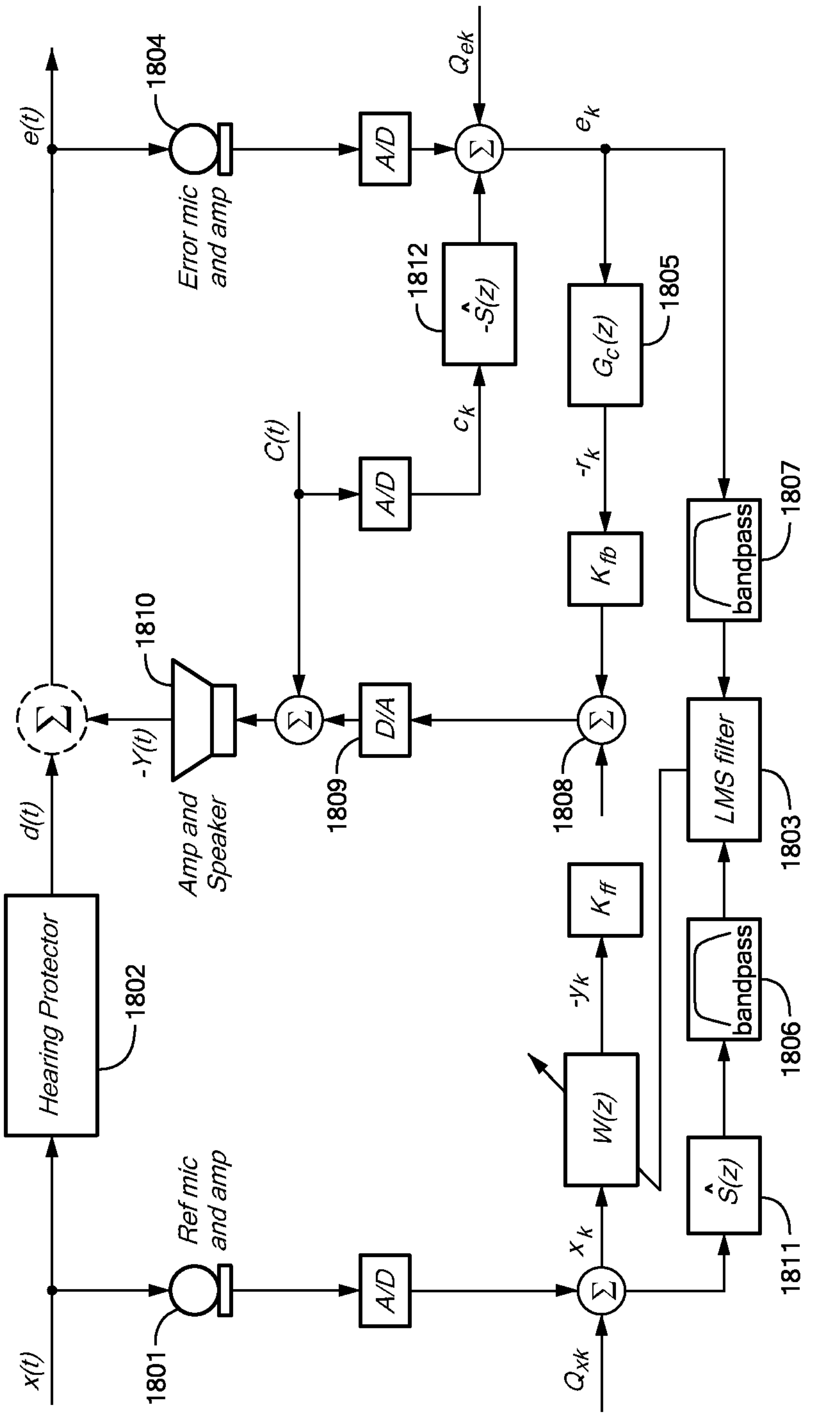
FIG. 18 shows a functional block diagram of the noise cancellation and communication feed-through systems for a single sound generator configuration.

FIG. 18 shows a schematic of an embodiment of one specific hybrid feed forward/feedback active noise reduction (ANR) system. In digital or analog feedback ANR, the cancellation path transfer function, which is a combination of the ANR speaker characteristics, cavity resonant behavior, and error microphone placement, limits the feedback gain in order to retain stability, and thus the level of active attenuation is limited. The incoming noise x(t) is measured by the external microphone 1801 of the hearing protector and is digitized as $x_k$. The past L samples of $x_k$ constitute the reference input $X_k$, where L is the filter length. Electronic and quantization noise enters as $Q_{xk}$. As x(t) passes through the hearing protector 1802 to become noise signal d(t), an LMS filter 1803 finds a weight vector, W(z), which is applied to $x_k$ to produce a cancellation signal $-y_k=W^TX_k$. An error microphone 1804 inside the hearing protector 1802 registers the error signal, which is digitized subject to noise $Q_{ek}$. $e_k$, along with $x_k$ filtered through $\hat{S}(z)$, adjusts the LMS filter 1803, and $e_k$ also passes through feedback compensator 1805, $G_c(z)$, which creates its own cancellation signal $-r_k$. Band pass filters 1806 and 1807 on $e_k$ and on $x_k$ filtered through $\hat{S}(z)$ focus noise cancellation energy on the band of interest and reject physiological noise. The two cancellation signals are scaled by gains $K_{fb}$ and $K_{ff}$, summed by summing node 1808, and digitized by D/A converter 1809. The cancellation signal is amplified and broadcast by output speaker 1810 as $-\hat{Y}(t)$ to sum with d(t) within the ear cup or earplug cavity. $\hat{S}(z)$ 1811 models the cancellation path response from the input voltage to the output speaker 1810 to output voltage of the error microphone 1804, as in a standard filtered-X LMS (FXLMS) algorithm, described, for example, in S. M. Kuo and D. R. Morgan, *Active Noise Control Systems*, John Wiley and Sons, 1996, incorporated herein by reference.

In one specific embodiment, the noise reduction algorithm is implemented on an Field-Programmable Gate Array (FPGA) as a state machine using VHSIC Hardware Description Language (VHDL) programming language. This allows reuse of the code for left and right channels so that the transistors can be reused, resulting in a smaller device with lower power consumption. Another embodiment is most aptly described as a combination of VHDL (to describe the DSP core and coprocessors) and assembly code (to describe the algorithm run on the DSP). With this embodiment, it was possible to rework the VHDL code architecture to get device utilization on a specific FPGA device down from nearly 100% to ~55%. VHDL is used to design a custom DSP core with co-processors for ADC read, DAC write, LMS, and vector products. This permits use of a smaller FPGA device and thus lower quiescent power consumption. The internal DSP is programmed via a custom assembly language and translated into machine code with an assembler developed specifically for this purpose. This embodiment marries the fast fixed-algorithmic abilities of state machines (e.g. the LMS coprocessor is pipelined to perform floating point multiplies, floating point add, and automatic RAM write-back every clock cycle with no DSP intervention) with the space-saving programmable abilities of a microprocessor core to control algorithm flow and to allow higher levels of abstraction over VHDL. While other embodiments might be implemented on other hardware platforms such as an ASIC, use of an FPGA allows implementation of additional functionality without changing the hardware, within the limits of the space and number of transistors on the FPGA. Implementation on an ASIC using VHDL, by contrast, locks in the module functions so that changes in functionality require redesign and refabrication of a new ASIC, which is time consuming and expensive. A programmable ASIC device can be embodied using the VHDL code to design a custom DSP core rendering a programmable ASIC if external flash memory is used to store the DSP program.

Figure 19:
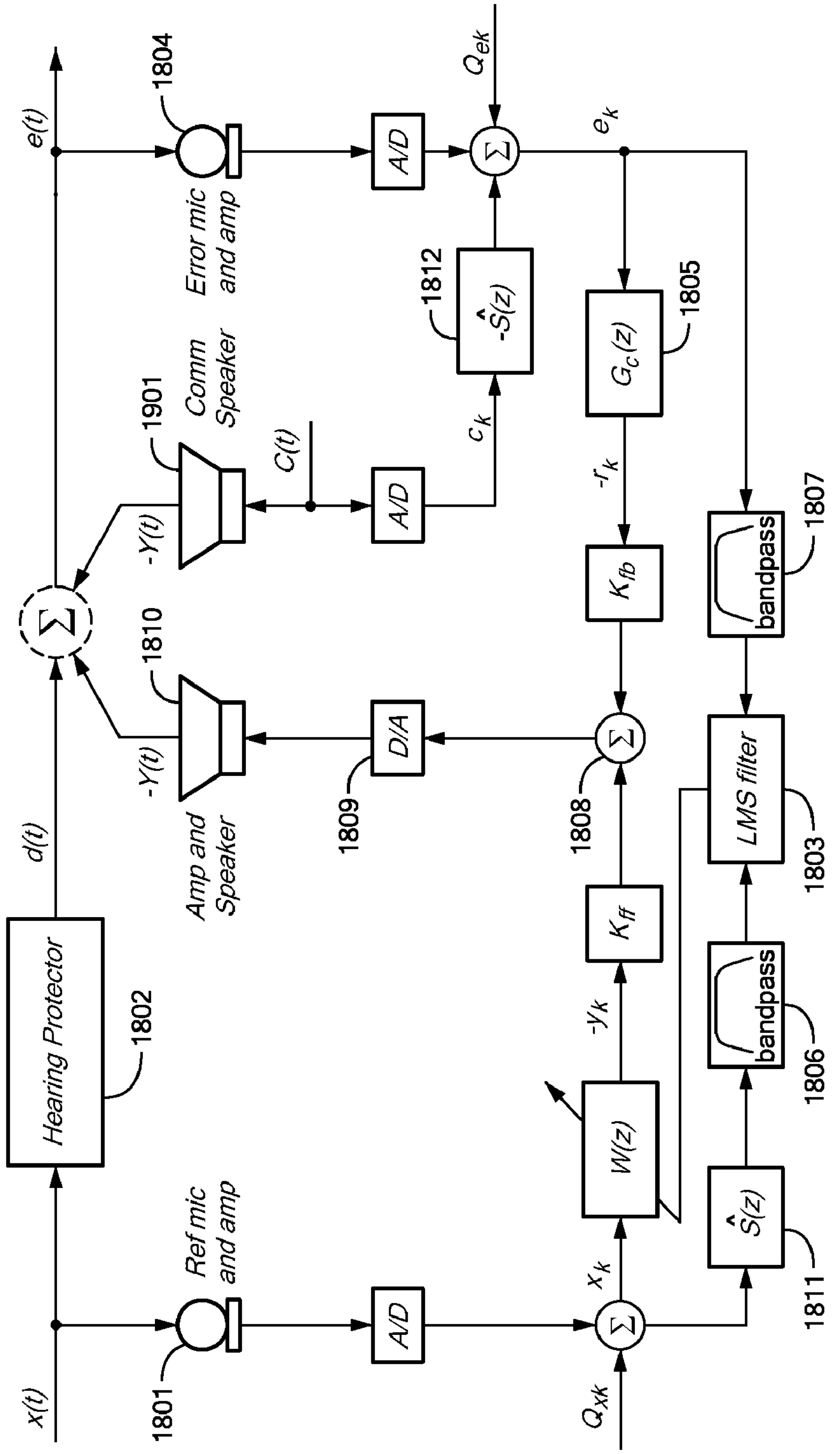
FIG. 19 shows a functional block diagram of the noise cancellation and communication feed-through systems for a dual sound generator configuration.

FIG. 18 is for the single sound generator configuration that delivers both cancellation and communication signals, though the architecture is easily modified for a dual speaker in-ear system as shown in FIG. 19, which includes a communications speaker 1901. When a communication signal C(t) is injected in FIG. 18 or FIG. 19, it is sampled and filtered through the communication path transfer function 1812. The result is subtracted from the measured error signal prior to ANR computations so that the residual $e_k$ entering the LMS filter and compensator is due to acoustic noise. C(t) is also passed through to the sound generator. This process minimizes cancellation of the communication signal along with the external noise and corruption of the LMS weight vector due to communication. Note that C(t) could serve as a reference input to the feedback loop in FIG. 18 such that it is passed through to the sound generator; however, this requires a closed-loop response with sufficient bandwidth to pass the signal. Note that if the same sound generator is used for noise cancellation and communication, then the communication and cancellation path transfer functions $\hat{S}(z)$ in FIGS. 18 and 19 are in principle identical. However, the embodiment can include distinct communication and cancellation path transfer functions and transfer function modeling components.

LMS filters direct energy equally to all noise bands, which, when operating on a sound field with very low frequency noise, can inhibit attenuation of noise at frequencies that are most desirable to attenuate and could also amplify noise in some bands, as energy is directed to attempt to cancel sound in frequency bands where the cancellation speaker is ineffective. In order to prevent this effect, the microphone signals are band passed. To prevent the weights from responding to frequency bands in which the noise cancellation speaker is ineffective, it is only necessary to filter the reference microphone signal going to the weight update calculation. However, in order to ensure convergence of the algorithm, the error microphone signal entering the weight update calculation must also be filtered. FIGS. 18 and 19 include the band pass filtering architecture. Pink noise and UH-60 noise are dominated by frequencies lower than the miniature cancellation speaker can deliver. Addition of the band pass filters de-emphasizes the low frequency content and causes the feed forward algorithm to focus on a frequency range where attenuation is possible.

Figure 20:
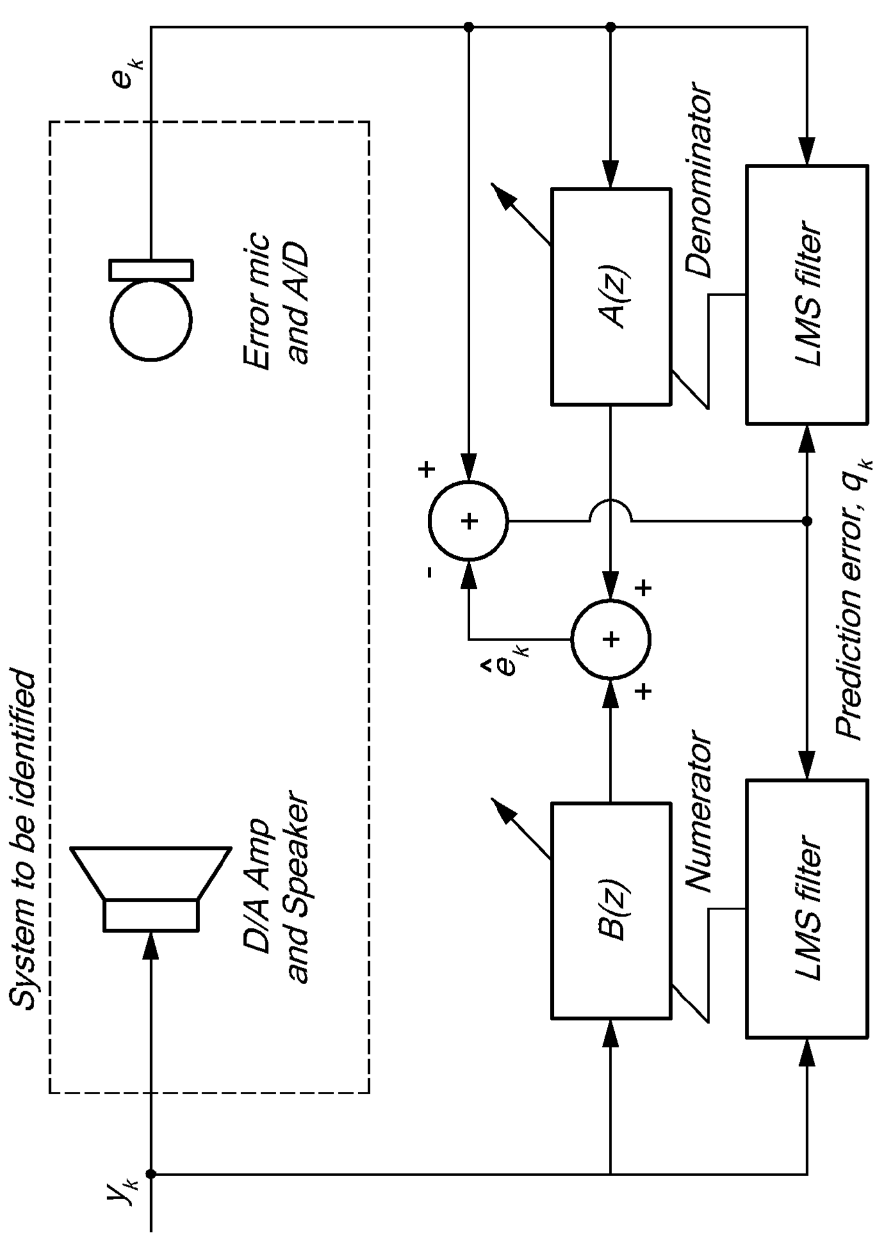
FIG. 20 shows a functional block diagram of an embodiment of automatic cancellation path response identification for the earplug.

Variability in the cancellation path and communication path responses 1811 and 1812 creates a need for a system with good stability margins, which poses a challenge for feedback and feed forward ANR individually. A frequency-dependent cancellation path gain is accommodated using an FXLMS filter as shown in FIG. 18 in which shaping filter 1811, $\hat{S}(z)$, shapes the reference input prior to the LMS filter update (see Kuo and Morgan, 1996). However, to the extent that the cancellation path varies from user to user, earplug to earplug, and insertion to insertion, the shaping filter 1811, $\hat{S}(z)$, needs either to be adaptive or robust to such variations. Similarly, the feedback system should also be robust to such variations. An adaptive cancellation path filter adds substantial computational requirements—up to double that of the system without a cancellation path model, while a fixed cancellation path filter does not avoid gain and phase errors over the variations evident from user to user. Therefore, this transfer function is identified as part of an initialization procedure performed after insertion of the earplug in the ear canal. FIG. 20 shows an embodiment of a cancellation path identification method that uses LMS filters to identify numerator and denominator of the cancellation path transfer function. Reuse of LMS filter code for cancellation path identification contributes to efficient implementation of the LMS identification method on an FPGA processor. The same procedure can be used to identify the communication path transfer function. Identified transfer functions may be coded in memory, or may be initialized upon reinsertion of the earplug.

The hybrid architecture provides a means to minimize performance degradation while building in adequate stability margins in the face of residual variations. The feedback compensator 1805, $G_c(z)$, provides a relatively low (5-10 dB) attenuation and effectively "flattens" the cancellation path response, such that the feedback compensated cancellation path gain is less variable than the open-loop gain. Feed forward ANR 1803 is based on a Lyapunov-tuned LMS (LyLMS) feed forward algorithm (U.S. Pat. No. 6,741,707, U.S. Pat. No. 6,996,241; which are incorporated herein by reference).

The cancellation path $\hat{S}(z)$ and communication path can be represented by either a finite-impulse response (FIR) or infinite-impulse response (IIR). An FIR filter introduces on the order of 2N multiplies—N multiplies each for filtering the sampled communication signal $c_k$, and reference input $x_k$, where N is the cancellation path filter length. In support of computational efficiency, a "black-box" IIR transfer path modeling approach can be embodied. The automated identification method provides a short white noise burst of moderate volume to the generator. The time-domain input and error microphone output data are processed using a fast linear identification technique (described, for example, in M. Q. Phan, J. A. Solbeck, and L. R. Ray, *A Direct Method For State-Space Model And Observer/Kalman Filter Gain Identification*, AIAA Guidance, Navigation, and Control Conf., Providence R.I., August 2004, incorporated herein by reference) referred to here as fastid. This approach, which is intended as an initialization routine, can provide high-fidelity, low-order IIR models for communication feed-through and filtered-X implementation, using as little as 0.1 second of input-output data. The process for automated modeling of the communication path response 1812 is identical.

The computation and memory requirements for fastid are relatively high since the algorithm requires inversion of a p(q+r)+r square matrix, where p is the order of the IIR filter, q is the number of outputs, and r is the number of inputs. One approach for IIR filter identification is the recursive least-squares (RLS) algorithm described, for example, by J.-N. Juang, *Applied System Identification*, PTR Prentice-Hall, Inc., 1994, incorporated herein by reference. The RLS algorithm begins with a set of IIR coefficients and updates them based on each new sample of input-output data until convergence. For a single-input, single-output system, the only non-scalar operations are 2×2 matrix inversions. The RLS model should be equivalent to that identified using fastid. However, the RLS algorithm requires significantly more time-series data to converge to a model of similar fidelity to the fastid method, as the fastid method benefits from having the entire time-series of input-output data available for identification. The fastid method determines the best-fit state-space model of the desired order based on a set of possibly noisy input-output data. The identified model is then transformed into a transfer function form. The algorithm requires the inversion of a very large data matrix; however, and alternative embodiments reduce such computational requirements.

An alternative identification algorithm can reuse the existing LMS algorithm and directly adapt the IIR model coefficients to the input-output data in real time, referred to herein as lmsid. It requires more input-output data than the fastid algorithm, but because it adapts the model in real time it does not take any longer to identify the model. One embodiment of the lmsid algorithm treats the numerator and denominator coefficients of the IIR model as elements of a single weight vector, and assembles the input and output histories into a single history vector in order to adapt the weight vector. Adaptation is otherwise identical to the feed forward ANR algorithm with a leakage factor dependent on signal strength and an adaptive step size, and the resulting models are valid down to around 50 Hz for 10 kHz sampling for a model order of 32. However, as the sample rate increases the low frequency divergence point also increases 50 Hz to 100 Hz, and impacts ANR performance.

Another embodiment of the lmsid algorithm separates the numerator and denominator coefficients into separate weight vectors and keeps the input and output histories separate for adapting the corresponding weight vectors. In addition, having an adaptive leakage factor in the ANR algorithm allows the weight vector to decay when there is no reference signal present. In the identification implementation, the presence of the reference signal (the identification signal, in this case) is guaranteed, so the leakage factor requirement is relaxed. The adaptive step sizes for the numerator and denominator coefficients are independent. This embodiment reduces the low-frequency divergence point, improves identified model consistency and translates to consistent ANR performance. A block diagram of the preferred lmsid embodiment is shown in FIG. 20.

Figure 21:
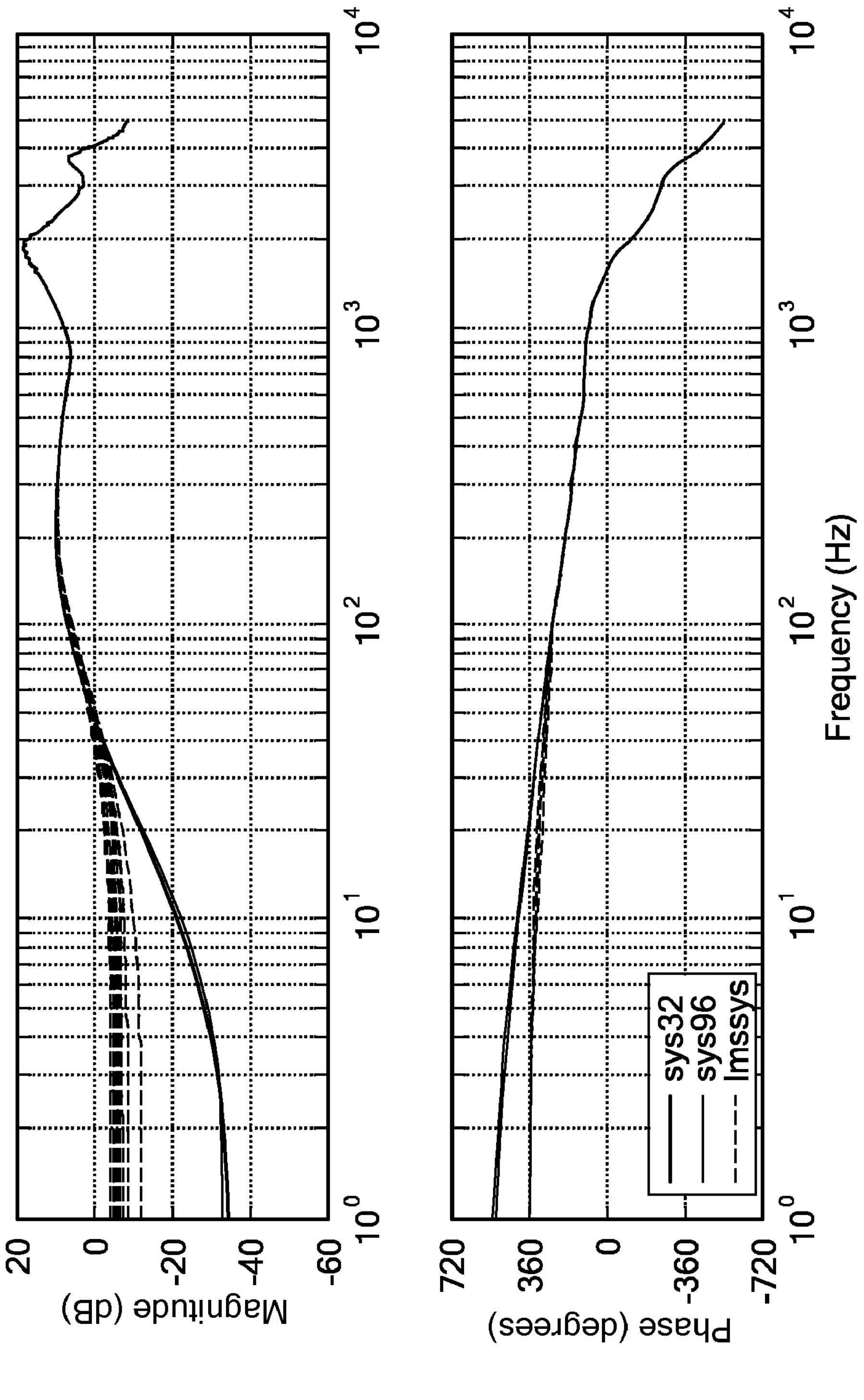
FIG. 21 shows the automatically-identified cancellation path response of an in-ear device (when sealed against the meatus) using a fastid and lmsid algorithms according to one embodiment.
Figure 22:
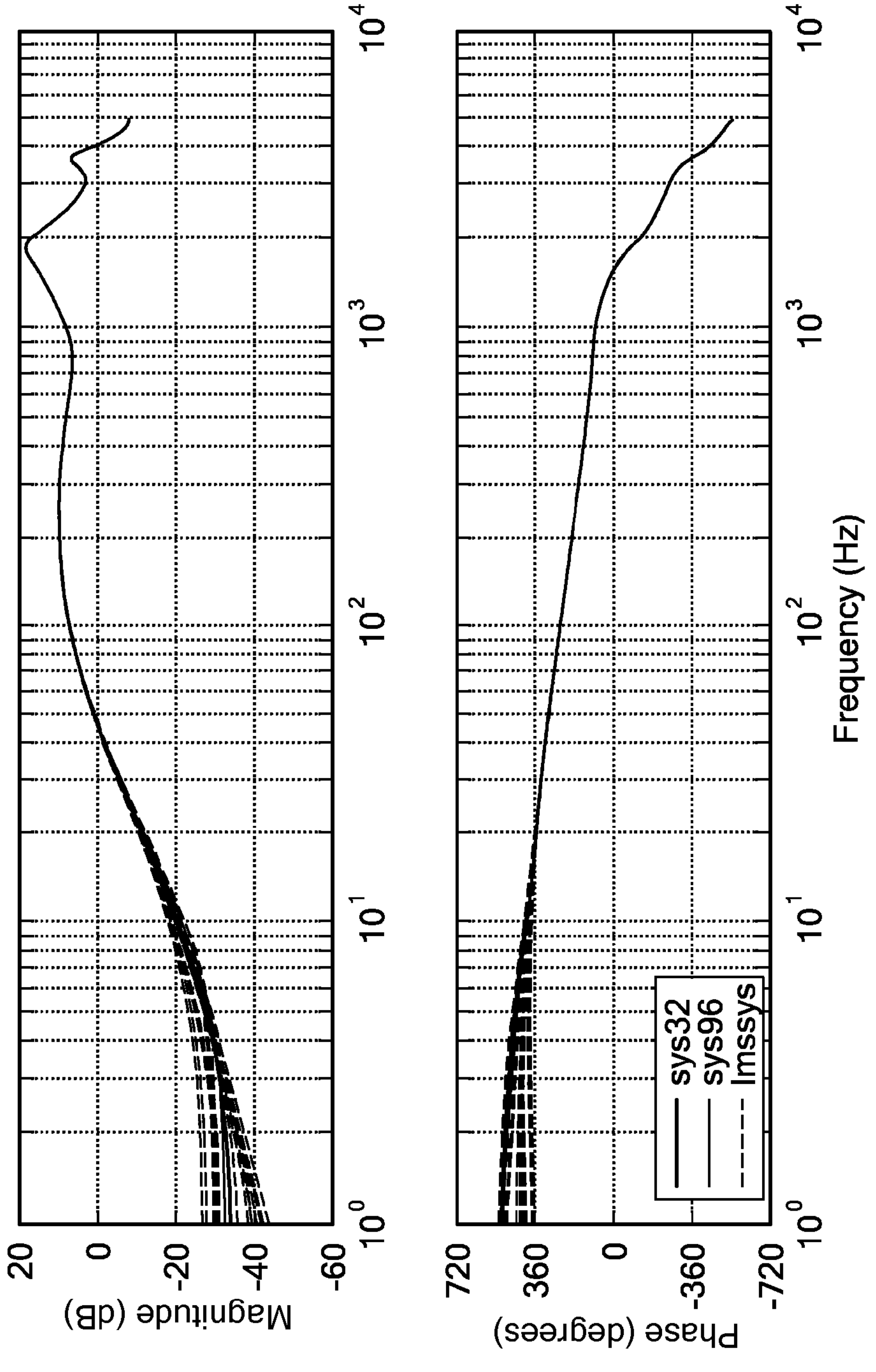
FIG. 22 shows a block diagram of a preferred embodiment of the lmsid algorithm for automatic identification of the cancellation and communication path transfer functions.

FIG. 21 shows a $96^{th}$ order model identified using fastid; and a $32^{nd}$ order model identified using fastid, in order to demonstrate the consistency of the fastid algorithm. Using the $96^{th}$ order model, twenty additional sets of input and output data are generated, and these are used with the two embodiments of lmsid to identify twenty $32^{nd}$ order IIR models each. The results of the first embodiment, in which coefficients of numerator and denominator are identified using a single LMS filter are shown in FIG. 21, and the results for the second embodiment, in which separate LMS filters are used to identify coefficients of numerator and denominator are shown in FIG. 22. The models identified using the first embodiment begin to diverge by 70 Hz and differ by around 15 dB from the truth model at 10 Hz. For the second embodiment, the models do not begin to diverge until 10 Hz and are within 10 dB of the truth model down to 1 Hz.

Figure 23:
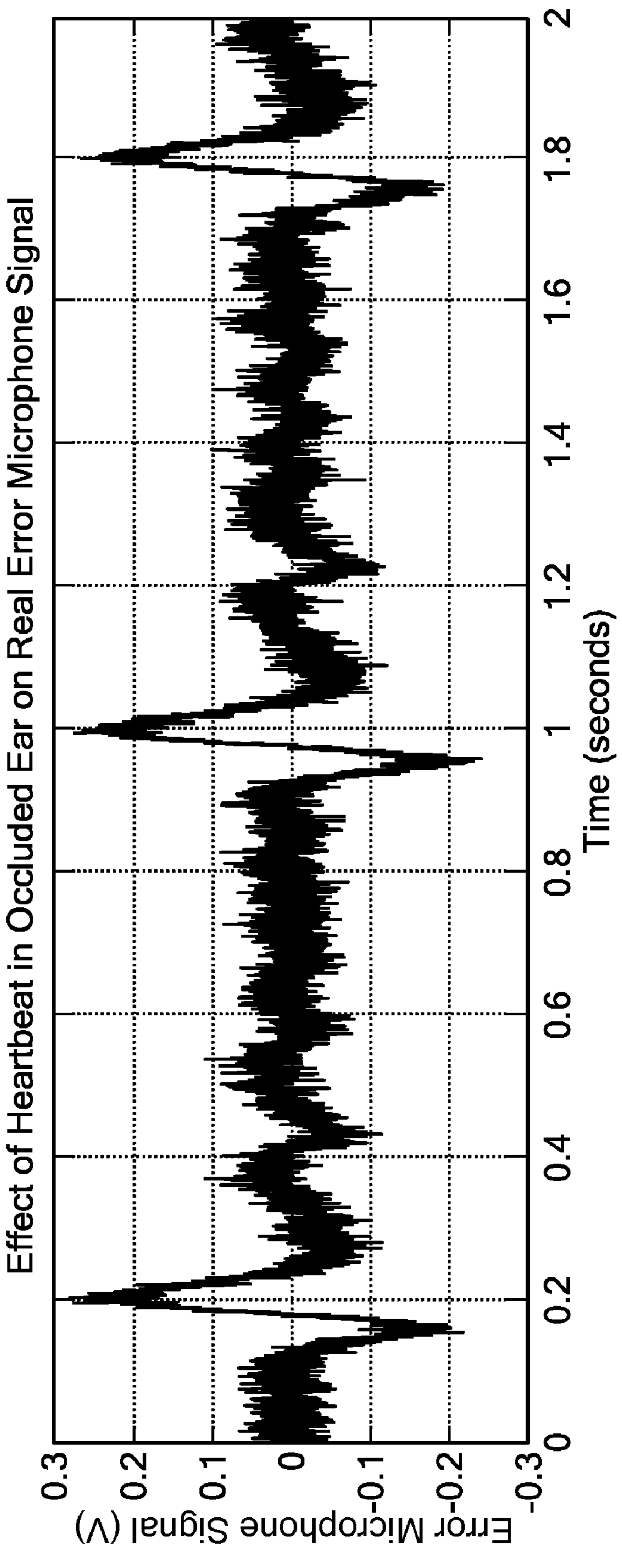
FIG. 23 shows a recording of the interior microphone signal during cancellation path identification with white noise excitation of 70-75 dB showing superimposed physiological noise.

When the in-ear device is inserted into a human ear, a signal resulting from the wearer's heartbeat may be superimposed over the identification signal at the error microphone. This heartbeat signal is of significant magnitude relative to the identification signal. FIG. 23 shows a recording of the internal microphone signal during excitation with an identification signal. The heartbeat has a period of 0.8 seconds (1.25 Hz or 75 bpm), but the significant waveform has a frequency of around 7 Hz. This heartbeat signal depends on the configuration and location of the internal microphone. The physiological heartbeat signal should be removed to retain fidelity of the identified model.

Figure 24:
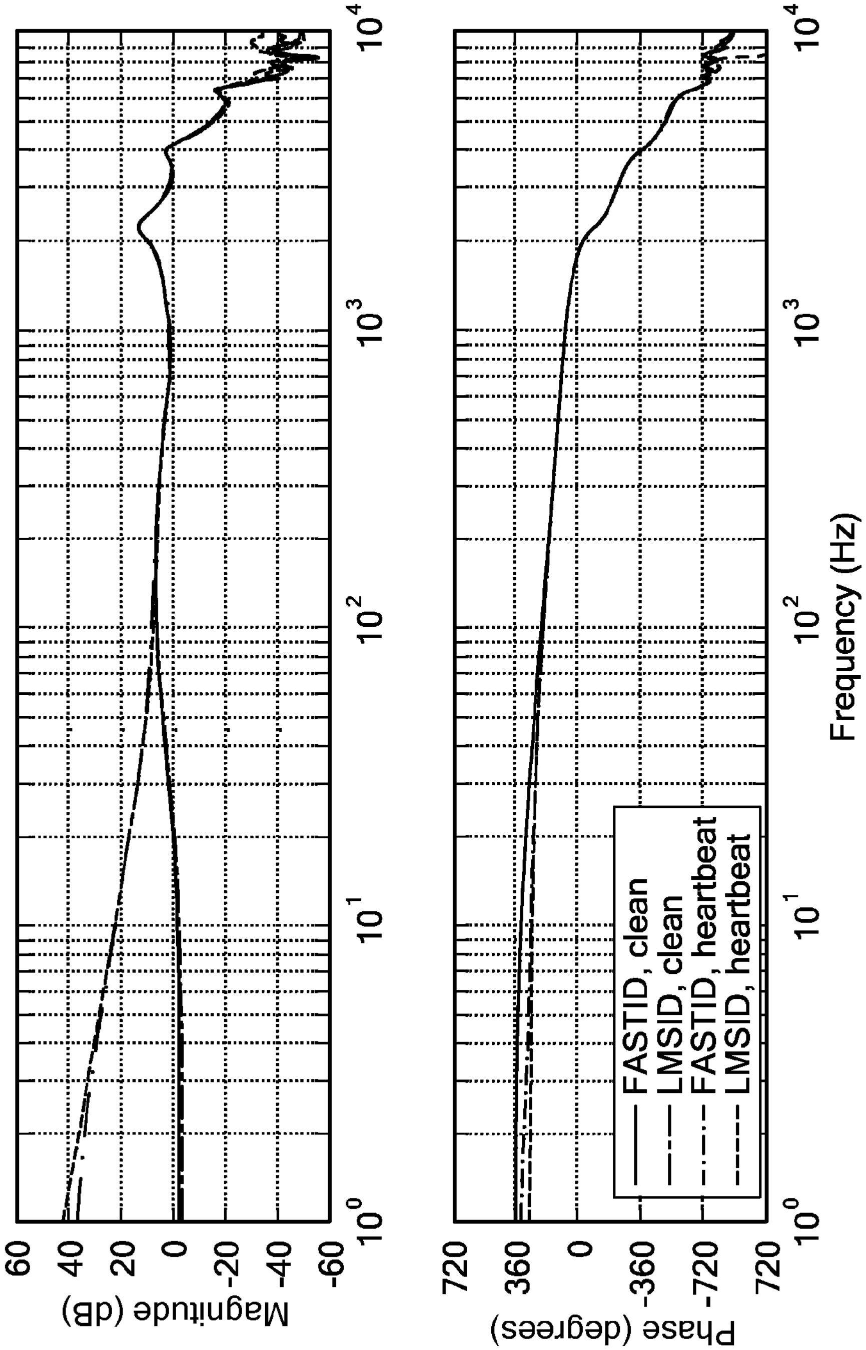
FIG. 24 shows the impact of the presence of the heartbeat on the identification of the cancellation path model using both fastid and lmsid algorithms according to an embodiment.
Figure 25:
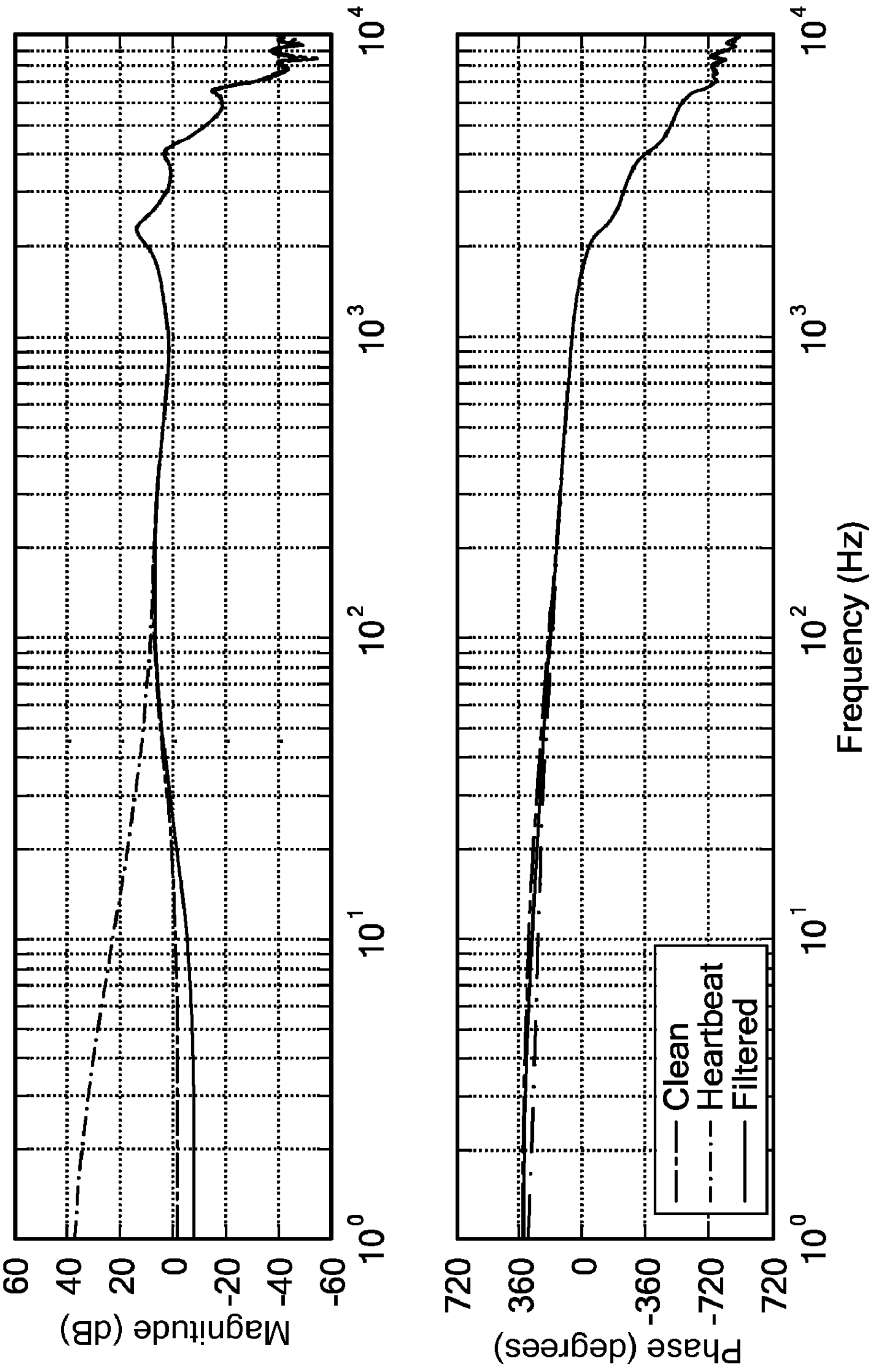
FIG. 25 shows results of cancellation path model identification using a fastid algorithm for clean and heartbeat-corrupted identification signals, and for the identification signal produced by filtering the heartbeat out of the corrupted signal.

FIG. 24 shows cancellation path responses identified using the fastid algorithm and an lmsid algorithm both with a simulated white noise signal and also with the same simulated white noise signal with simulated physiological noise superimposed having a characteristic frequency as measured. At high frequencies, above 100 Hz, there is little or no effect of physiological noise on the identified model. Below 100 Hz, the models resulting from heartbeat-corrupted identification data display a much higher magnitude due to heartbeat-induced low frequency energy at the error microphone. The heartbeat has a period of roughly 0.8 seconds (1.25 Hz), and the major waveform of the heartbeat has an approximate frequency of 7 Hz, but the identified models are not capable of such detail at low frequencies, so the effect is spread across low frequencies. A 20 Hz $2^{nd}$-order Butterworth high pass filter is employed to remove the physiological noise with four passes (equivalent of an $8^{th}$ order filter) required for complete removal. To prevent phase shift induced by filtering, both the cancellation speaker excitation signal and the error microphone response are filtered so as to induce the phase shift in both the input and output data to the identification method. FIG. 25 shows the results of this approach for an identified model order of 32. The filter recovers the truth model, with only a slight magnitude discrepancy at low frequencies.

Figure 26:
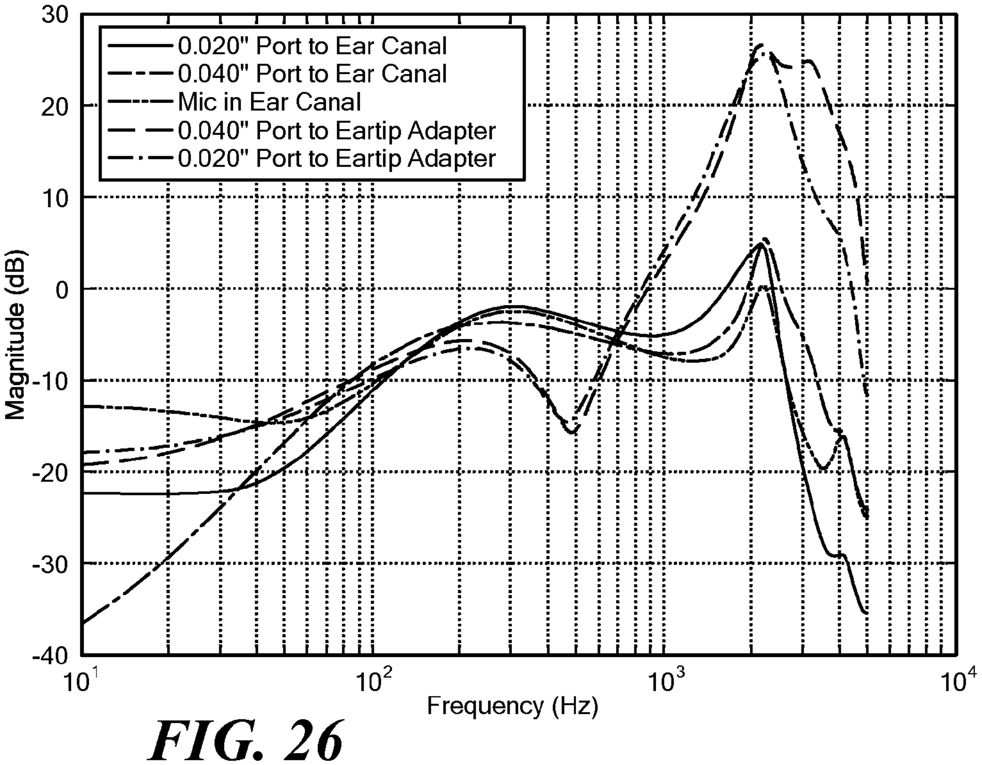
FIG. 26 shows representative cancellation path responses for four embodiments of an embodiments or error microphone placement with respect to the ear canal according to embodiments of FIG. 8, compared with the cancellation path response for an error microphone placed in the ear canal.

Coupling of the error microphone affects the cancellation path response which in turn affects feedback ANR performance. A flat cancellation path response is desirable for design of the ANR feedback compensator 1805, $G_c(z)$, in FIG. 18. A configurable experimental in-ear device was assembled from loose components comprised of a sound generator, an internal microphone, a foam ear tip and an ear tip adaptor. Coupling configurations between the internal microphone and sound generator were studied to determine the preferred embodiment of the coupling between the sound generator and internal microphone. Studies included i) coupling the error microphone to the ear tip adapter using 0.040 inch inner diameter (ID) Tygon tubing of varying lengths, ii) coupling using 0.020 inch ID Tygon tubing also of varying lengths, iii) placing the error microphone within the occluded space directly, iv) coupling the microphone to the occluded ear canal using a 0.040 inch×0.6 inch (15 mm) probe tube inserted along the side of the ear tip, and v) a similar configuration using a 0.020 inch×0.6 inch port inserted along the side of the ear tip. FIG. 26 shows the cancellation paths identified by these experiments showing that that coupling the error microphone to the occluded ear canal using a probe tube provides an effective substitute for microphone location, reducing a node at roughly 480 Hz and the resonance at roughly 2200 Hz. FIG. 9 shows a cross-sectional view of an embodiment of an ear tip adapter 106 designed based on the outcome if this experiment. It provides an integral port through the ear tip 108 for the internal microphone, a socket for direct internal microphone attachment, and a means of retaining the external microphone at the rear of the earplug.

Figure 27:
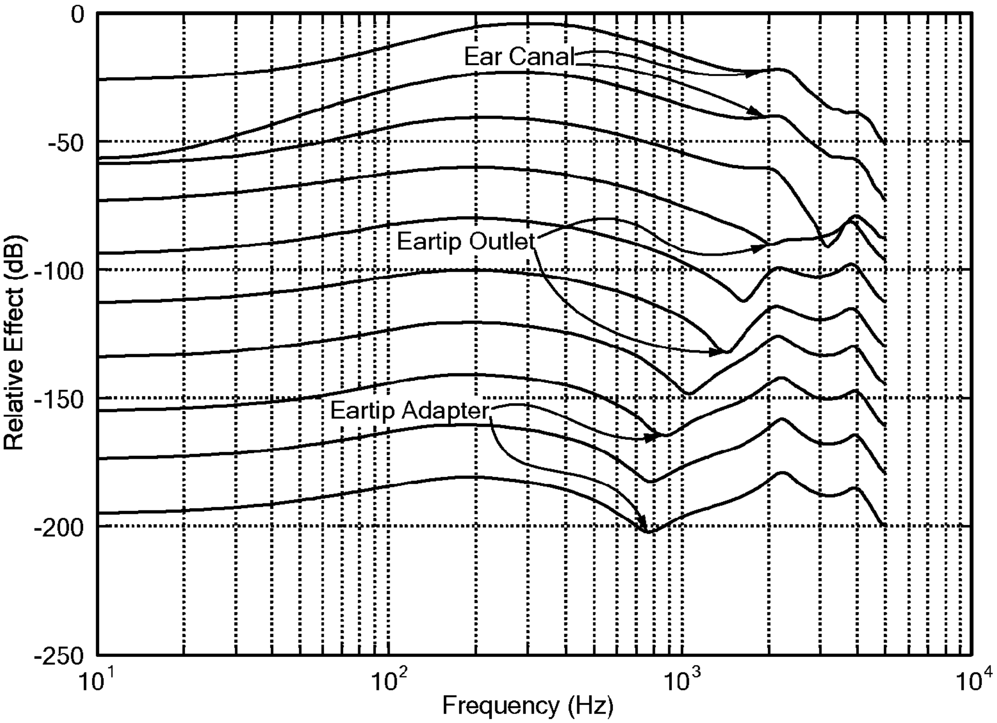
FIG. 27 shows the relative effect of interior microphone probe placement within a prototype embodiment so as to select interior microphone probe tube length.

The way that the internal microphone is coupled to the ear canal also has a large effect on the shape of the cancellation path, which, in turn, significantly affects ANR performance. A series of experiments were carried out placing the internal microphone probe at different points within a configurable earplug. As shown in FIG. 27, the location of a node in the cancellation path can be moved relative to the band of interest for ANR by varying the error microphone probe insertion location.

Figure 28:
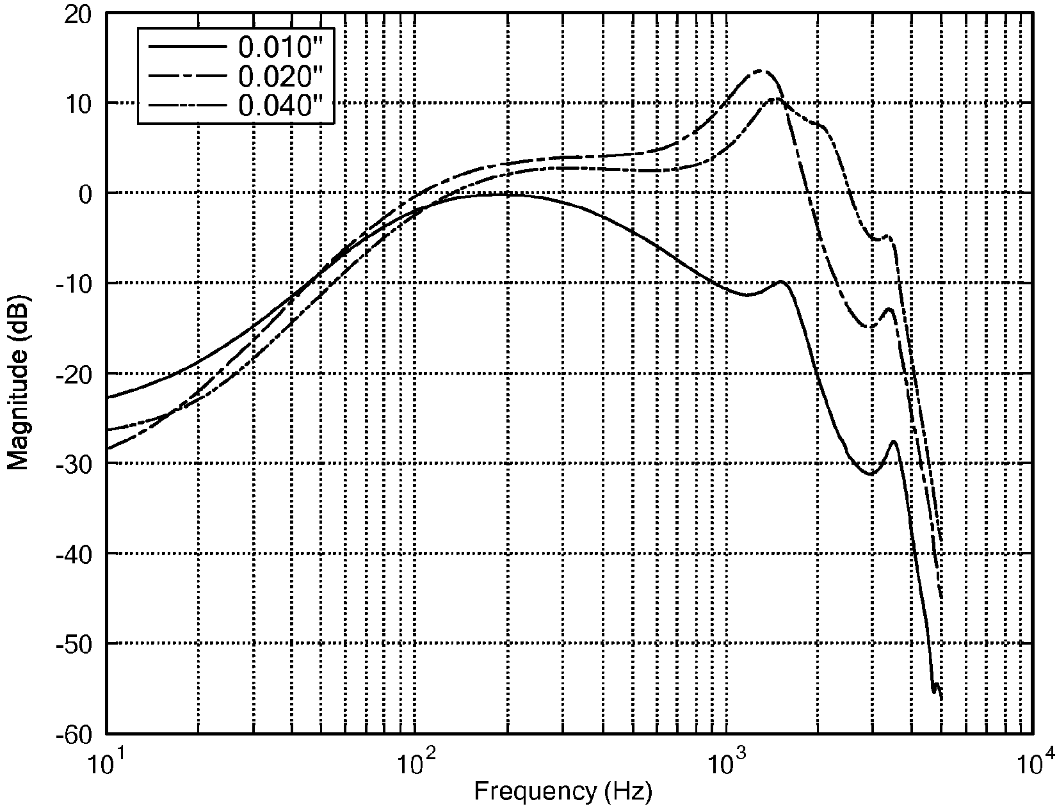
FIG. 28 shows the cancellation path transfer functions recorded using 0.010 inch, 0.020 inch, and 0.040 inch diameter Tygon tubing to couple the error microphone to the ear canal volume.

The effect of internal microphone probe tube inner diameter on the cancellation path transfer function was also studied using the configurable earplug. The cancellation sound generator was coupled to the interior of the ear canal volume with a 20 mm length of 0.020 inch ID Tygon tubing. The internal microphone was then coupled to the ear canal volume using 0.010 inch, 0.020 inch, and 0.040 inch ID Tygon tubing. The cancellation paths recorded for each configuration are shown in FIG. 28, which shows that the interior microphone probe tubing acts as a low-pass filter on the interior microphone signal. Tubing diameter can be tuned to move the upper corner frequency higher (larger diameter tubing) or lower (smaller diameter tubing). At diameters much below 0.010 in, too much signal in the band of interest for ANR is attenuated. The resonances observed at roughly 1300 Hz and 3300 Hz are attributed to the sound generator, and low-frequency roll-off is attributed to the response characteristics of both the speaker and microphone.

Figure 29A:
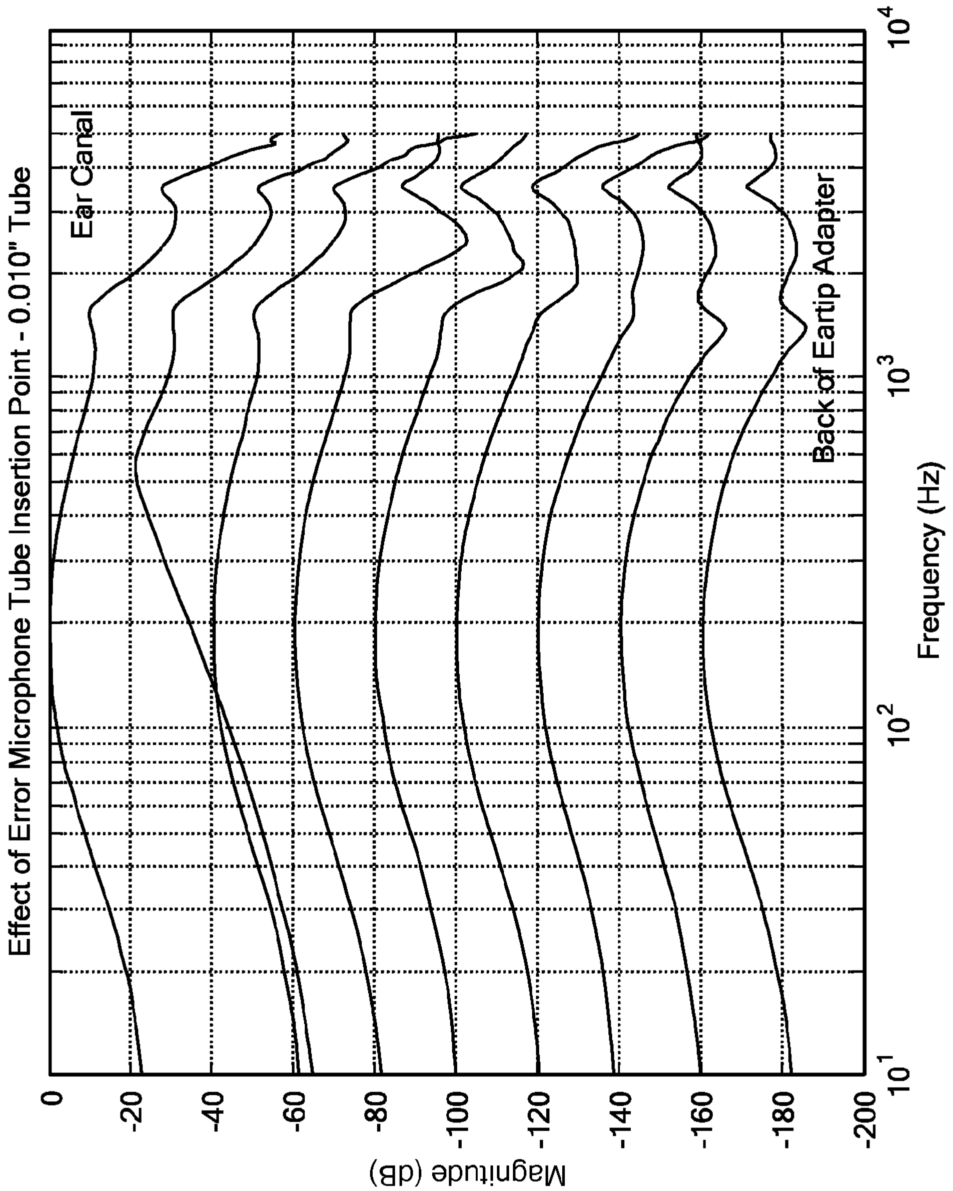
FIG. 29 shows cancellation path transfer function evolution as the interior microphone probe tube is drawn from the ear canal volume back into the ear tip for 0.010 inch tubing (top), 0.020 inch tubing (middle), and 0.040 inch tubing (bottom) showing migration of a prominent transfer function node with probe size.
Figure 29B:
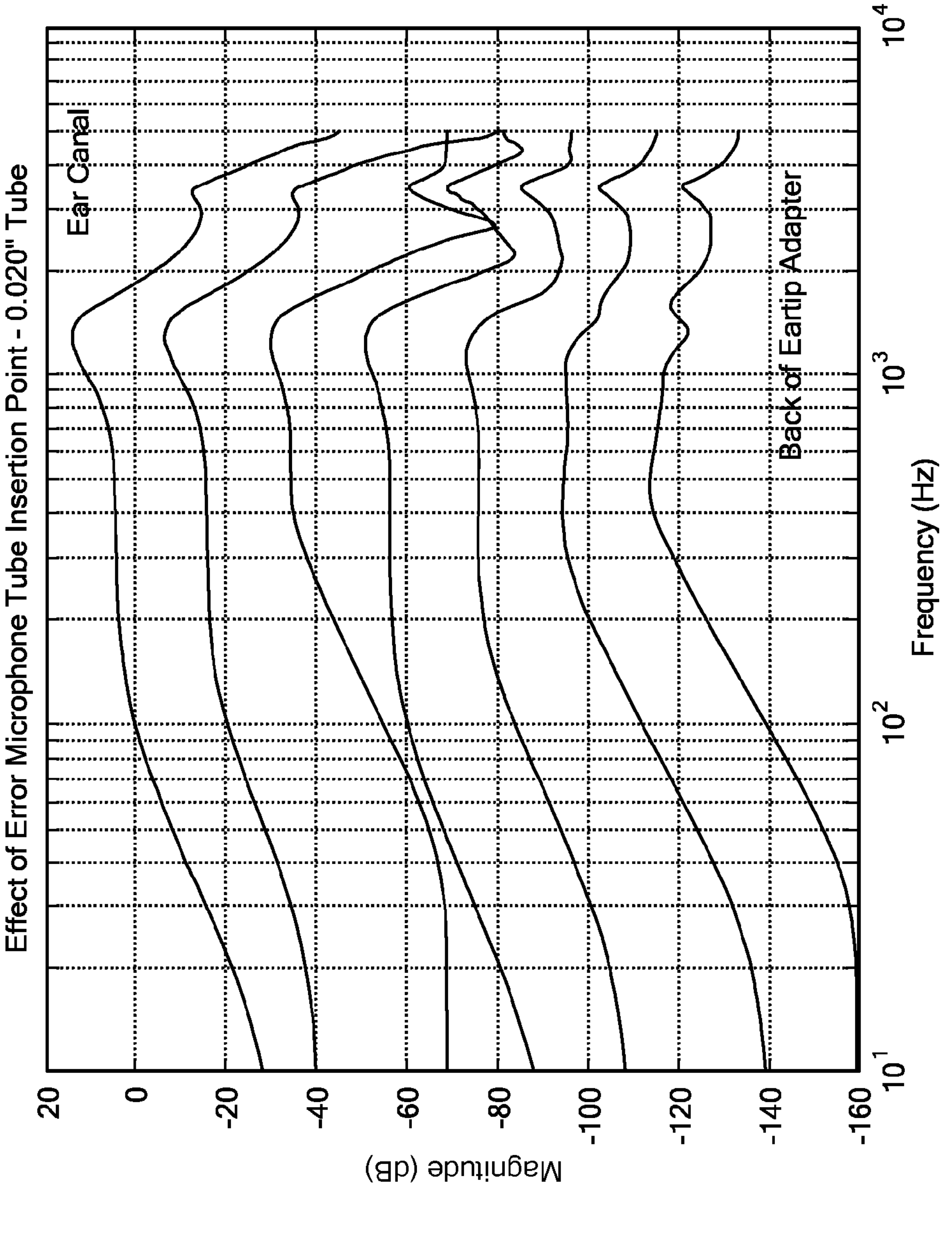
Figure 29C:
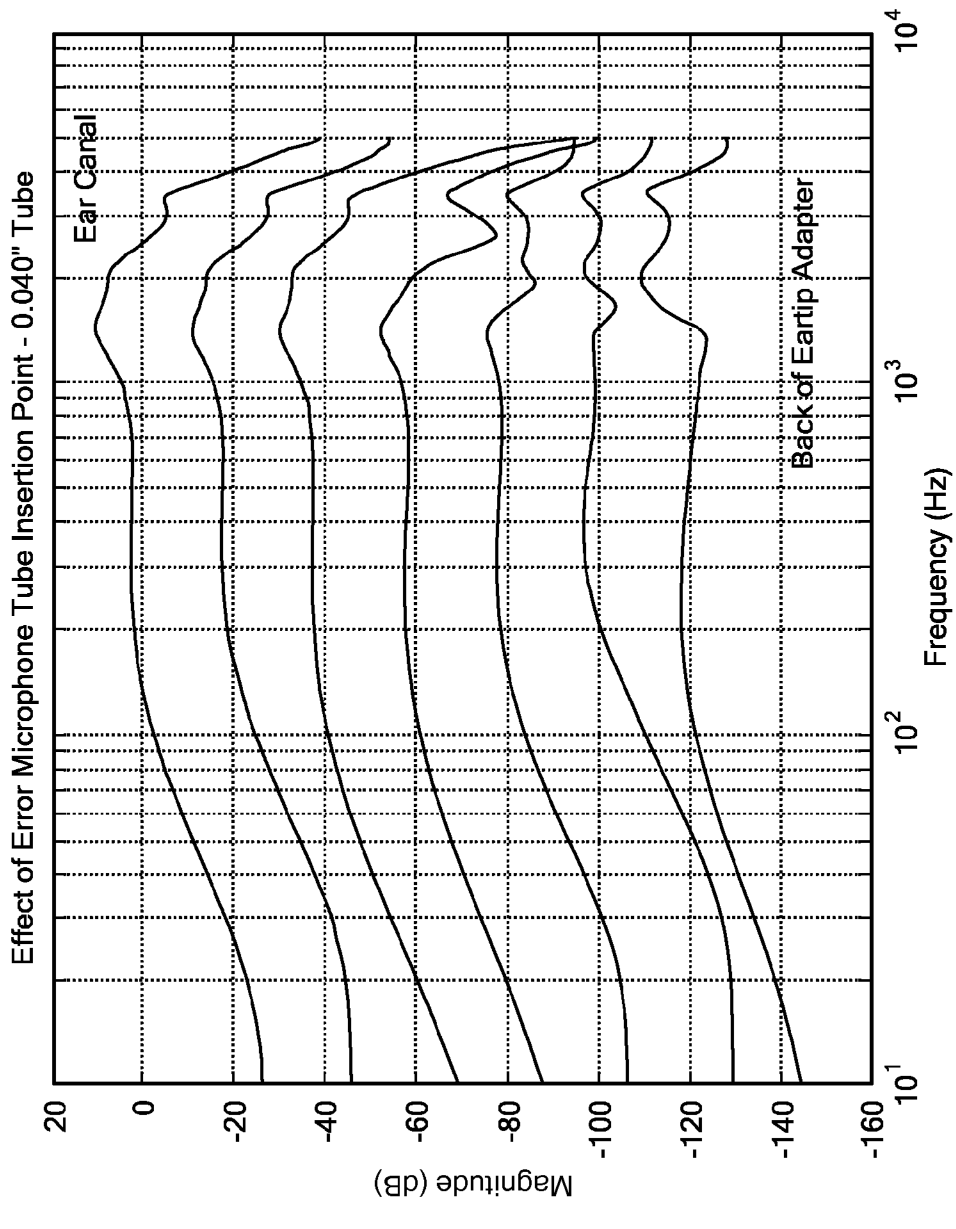

In conjunction with evaluating the effect of probe diameter, probe location along the ear tip orifice was evaluated with each diameter of the probe tube. The evolution of the cancellation path transfer function, as the probe is traversed backward from the ear canal through the ear tip, is shown in FIG. 29. A recurring node in the transfer function, common to all of the probe diameters, moves from higher frequency (approximately 2.5 kHz) in the ear canal to lower frequency (approximately 1.3 kHz) at the rear of the ear tip. This node can be attributed to the geometry of the ear tip orifice or the ear canal volume, but is relatively independent of probe tube size.

Embodiments of the ear tip 108 and ear tip adaptor 106 in FIGS. 3-7 accommodate the ability to embody various configurations of internal microphone placement, ear tip inner diameter, and probe tube inner diameter and length. The ear tip adaptor 106 can include exterior threads to accommodate a replaceable threaded ear tip or a smooth adaptor can be employed. Both silicone flanged ear tip and foam ear tips are accommodated.

Figure 30:
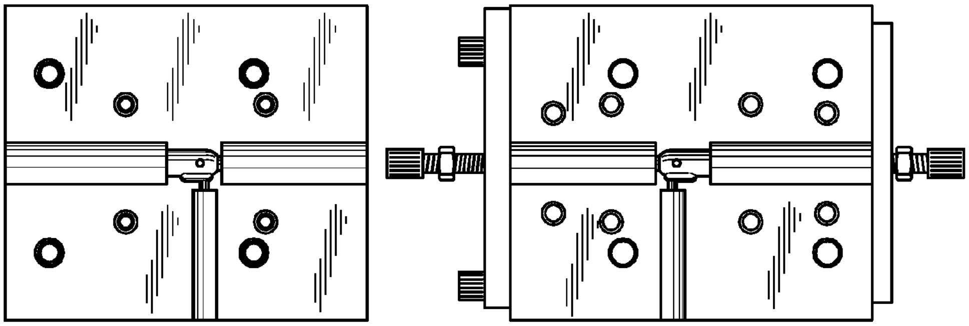
FIG. 30 shows an embodiment of the tooling for manufacturing an in-ear device with single sound generator using low temperature and pressure injection molding.
Figure 31:
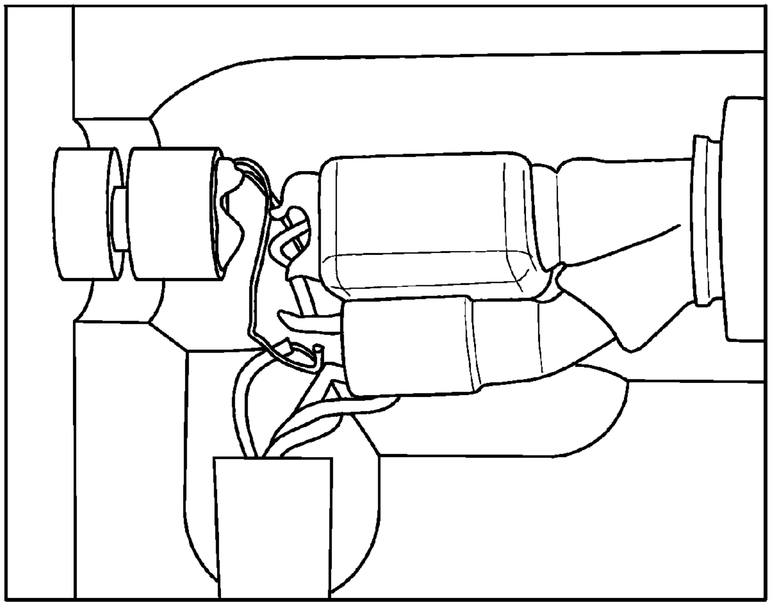
FIG. 31 shows an embodiment of the tooling for manufacturing an in-ear device with two sound generators using low temperature and pressure injection molding.

A low-temperature, low-pressure injection molding process is employed to mold plastic around the microphones and sound generators, and around the portion of the ear tip adaptor that interfaces with these components, embedding it into the plastic according to the designed geometry. FIG. 30 shows an embodiment of the mold cavity and the relative locations of the parts within the mold cavity for the single sound generator configuration, and FIG. 31 shows an embodiment of the mold cavity and the relative locations of the parts within the mold cavity for the dual sound generator configuration. Parts are held in place using mold inserts. The interior microphone is held in place by cementing it to the sound generator and coupled to the ear tip adapter using a piece of flexible tubing. Fixturing aids in protecting electronic components during injection molding. Parts are wired before molding, and molding over the wiring harness provides strain relief.

Figure 32:
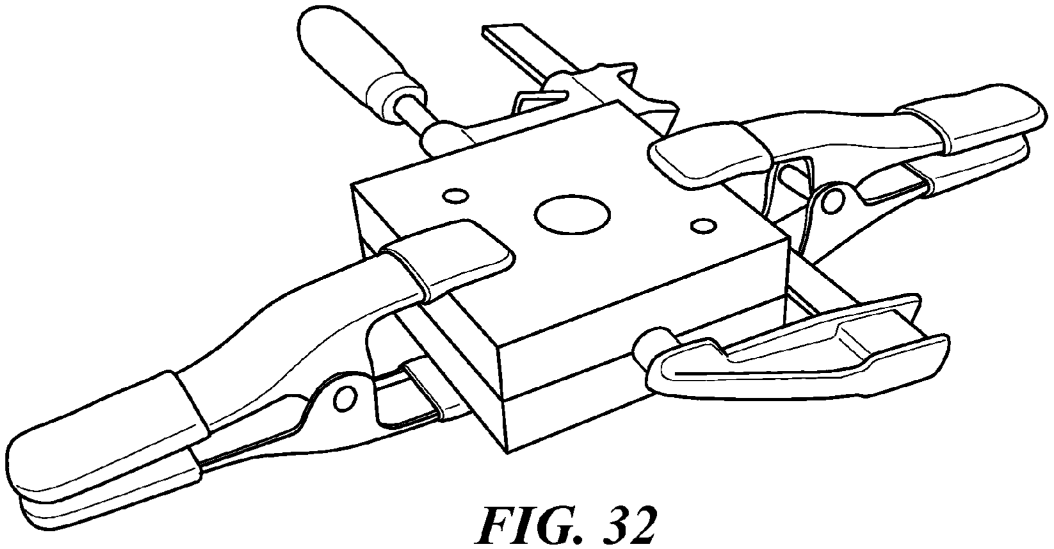
FIG. 32 shows an embodiment of the tooling for manufacturing including the closed mold and fixturing.
Figure 33:
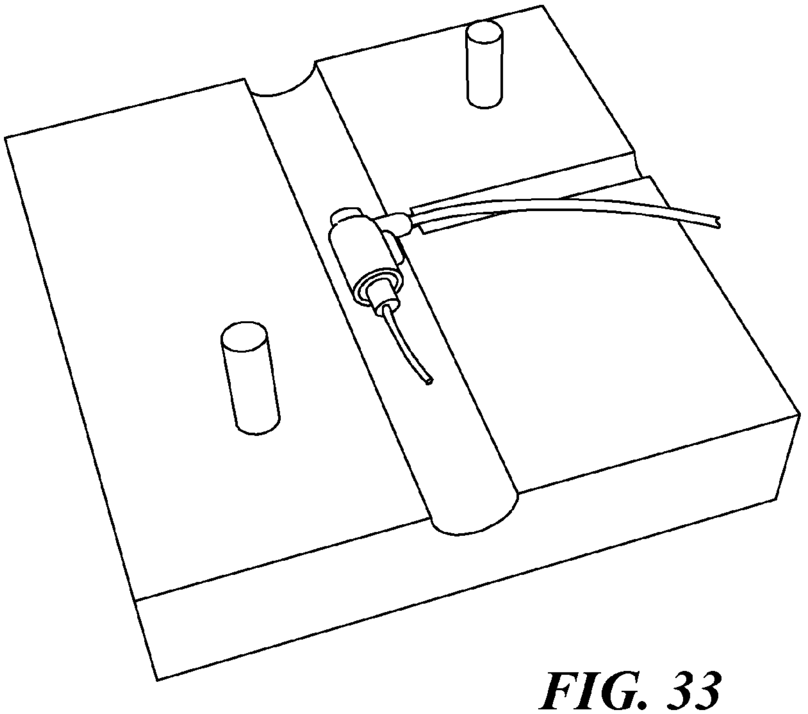
FIG. 33 shows a finished in-ear device after injection molding.

The mold halves are oriented with respect to one another using four dowel pins and retained with four cap screws as shown in FIG. 32. An additional four threaded holes in the top half of the mold accommodate jack screws if necessary to separate two halves after molding. Cylindrical mold inserts hold the exterior microphone and ear tip adapter in place and help form the shape of the front and rear of the plug. They are retained in the mold using a plate on either side. FIG. 33 shows the finished in-ear device after the molding process. This manufacturing technique is highly amenable to the transition from laboratory bench to small-scale production.

Manufacturing of the earplug is performed using a low-temperature, low pressure injection molding process by which sound generators and internal microphone, secured to the ear tip adaptor are located in the mold using a fixture, and external microphone is located in the mold using a fixture, with all components wired and connected to the wiring harness. Plastic material injected into the mold flows around components and wiring harness, encapsulating components and providing strain relief to the wiring harness. Fixtures protect the electronic components during molding.

Various aspects of embodiments of the invention may be implemented in any conventional computer programming language. For example, preferred embodiments may be implemented in a procedural programming language (e.g., "C" or the VHDL Hardware Description Language) or an object oriented programming language (e.g., "C++", Python). Alternative embodiments of the invention may be implemented as pre-programmed hardware elements, other related components, or as a combination of hardware and software components.

Various aspects of embodiments can be implemented as a computer program product for use with a computer system. Such implementation may include a series of computer instructions fixed either on a tangible medium, such as a computer readable medium (e.g. a diskette, CD-ROM, ROM, or fixed disk) or transmittable to a computer system, via a modem, serial or other interface device, such as a communications adapter connected to a network over a medium. The medium may be either a tangible medium (e.g. optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A noise canceling and communication system comprising:

an in-ear device adapted to fit in an ear canal of a device user and having:

i. a passive noise reduction element for reducing external noise entering the ear canal, ii. at least one external microphone for sensing an external acoustic signal outside the ear canal to produce a representative external microphone signal, iii. at least one internal microphone for sensing an internal acoustic signal proximal to a tympanic membrane to produce a representative internal microphone signal, iv. at least one internal sound generator for producing a noise cancellation signal and an acoustic communication signal, both directed towards the tympanic membrane, and v. at least one probe tube for shaping an acoustic response between the internal sound generator and the internal microphone to be relatively constant over a wide audio frequency band; and an external electronics module in communication with the in-ear device for processing the microphone signals using a hybrid feed forward and feedback active noise reduction algorithm to produce the noise cancellation signal, the noise reduction algorithm including at least one noise modeling component based on a transfer function associated with the internal sound generator and at least one of the microphones to automatically adjust the noise cancellation signal for fit and geometry of the ear canal of the user.

2. A system according to claim 1, wherein the electronics module further passes the communication signal to at least one internal sound generator.

3. A system according to claim 1, wherein the electronics module further includes a communications modeling component based on a transfer function associated with at least one internal sound generator and at least one microphone to subtract the communication signal from the signal sensed by the internal microphone.

4. A system according to claim 1, wherein the noise reduction algorithm further rejects physiological or voice generated noise present in the ear canal.

5. A system according to claim 1, wherein the noise reduction algorithm includes a band pass filtering component for directing acoustic energy of the noise cancellation signal to selected frequency bands.

6. A system according to claim 1, wherein the noise reduction algorithm is implemented on a Field-Programmable Gate Array (FPGA) as a state machine using VHSIC Hardware Description Language (VHDL) programming language.

7. A system according to claim 1, wherein the noise reduction algorithm is implemented with a combination of VHSIC Hardware Description Language (VHDL) programming language and assembly code.

8. A system according to claim 1, wherein the at least one probe tube includes a probe tube outlet which is replaceable so as to keep the probe tube free of cerumen.

9. A system according to claim 1, wherein the at least one probe tube is acoustically isolated from the at least one internal sound generator.

10. A system according to claim 1, wherein the at least one internal microphone is acoustically isolated from at least one internal sound generator.

11. A system according to claim 1, further comprising:

a noise exposure sensing module for determining a time-weighted noise exposure of the device user.

12. A system according to claim 1, wherein the in-ear device includes a molded plastic device housing encapsulating electronic components of the in-ear device.

13. An in-ear communication device adapted to fit in an ear canal of a device user, the device comprising:

a passive noise reduction element fitting in the ear canal of the user for reducing external noise entering the ear canal;

at least one sensing element for generating a sensing data signal associated with the ear canal;

at least one internal sound generator for producing an acoustic communication signal directed towards a tympanic membrane;

a probe tube having one end coupled to the sensing element and the other end having a probe tube outlet proximal to the tympanic membrane for shaping an acoustic response between the internal sound generator and the sensing element; and an external electronics module in communication with the in-ear device for processing at least one microphone signal to produce an enhanced communication signal, the processing algorithm including a modeling component based on a transfer function associated with the internal sound generator and at least one of the microphones to automatically detect fit and geometry of the ear canal of the user.

14. A device according to claim 13, wherein the modeling component is used to shape an acoustic communication signal directed towards the tympanic membrane.

* * * * *